US005176737A

United States Patent [19]
Chrystal et al.
[11] Patent Number: 5,176,737
[45] Date of Patent: Jan. 5, 1993

[54] BENZISOXAZOLE COMPOUNDS USEFUL AS HERBICIDES

[75] Inventors: Ewan J. T. Chrystal, Wokingham; John E. D. Barton; David Cartwright, both of Reading; Christopher J. Mathews, Maidenhead, all of England

[73] Assignee: Imperial Chemical Industries PLC, London, United Kingdom

[21] Appl. No.: 652,705

[22] Filed: Feb. 7, 1991

[30] Foreign Application Priority Data

| | | | |
|---|---|---|---|
| Feb. 16, 1990 | [GB] | United Kingdom | 9003557 |
| Nov. 5, 1990 | [GB] | United Kingdom | 9023985 |

[51] Int. Cl.[5] .................. C07D 261/02; C07D 413/06; A01N 43/40

[52] U.S. Cl. .................................... 504/252; 544/111; 546/210; 546/270; 548/241; 504/193; 504/271; 504/250; 504/225; 504/248; 504/249

[58] Field of Search ...................... 548/241; 71/88, 94; 546/270, 210; 544/111

[56] References Cited

U.S. PATENT DOCUMENTS

| | | | |
|---|---|---|---|
| 4,571,225 | 2/1986 | Nielsen | 71/88 |
| 4,888,041 | 12/1989 | Jackson et al. | 71/88 |
| 4,898,874 | 2/1990 | Walsh et al. | 548/241 |

FOREIGN PATENT DOCUMENTS

| | | | |
|---|---|---|---|
| 178708 | 4/1986 | European Pat. Off. | 548/241 |
| 193700 | 9/1986 | European Pat. Off. | 548/241 |
| 299446 | 1/1989 | European Pat. Off. | 548/241 |
| 2192878 | 1/1988 | United Kingdom | 548/241 |
| 2192879 | 1/1988 | United Kingdom | 548/241 |

*Primary Examiner*—Mary C. Lee
*Assistant Examiner*—Joseph K. McKane
*Attorney, Agent, or Firm*—Joel G. Ackerman

[57] ABSTRACT

A herbicidal compound of formula (I):

(I)

in which

Ar is an optionally substituted aryl or heterocyclic ring system:

$R^1$ and $R^2$ are independently selected from H, optionally substituted alkyl, alkenyl or akynyl, halogen, $NR^aR^b$, or $R^1$ and $R^2$ together with the carbon to which they are attached form an optionally substituted alkenyl or cycloalkyl group;

$R^3$ is $CO_2R^4$, CN, $COR^4$, $CH_2OR^4$, $CH_4(OH)R^4$, $CH(OR^4)R^5$, $CH_2OSO_6R^4$, $CH_2OSO_6R_4$, $CH_2ONR^6R^7$, $CSNH_2$, $COSR^4$, $SCOR^4$, $COHNSO_2R^4$, $CONR^6R^7$, $CONHNR^6R^7$, $CONHN^+R^6R^7R^8$ $Y^{-2}$, $CO_2^-M^+$ or $COON{=}CR^6R^7$;

$M^+$ is an agriculturally acceptable cation;

$Y^-$ is an agriculturally acceptable anion;

$R^4$, and $R^5$ are independently selected from H or an optionally substituted alkyl, aryl, alkenyl or alkynyl group;

$R^6$, $R^7$, $R^8$, $R^9$, $R^a$ and $R^b$ are independently selected from H or an optionally substituted alkyl alkenyl, aryl or akynyl group or any two of $R^6$, $R^7$, $R^8$, $R^9$, $R^a$ and $R^b$ together with the atom to which they are attached form a cycloalkyl or heterocyclic ring;

$R^6$ and $R^7$ may also be a heterocyclic ring;

W is O or $NR^{10}$ where $R^{10}$ is H or lower alkyl;

X is $(CH_2)_n$, CH=CH, $CH(OR^c)CH_2$, $COCH_2$;

where $R^c$ is H or an optionally substituted alkyl, aryl, alkynyl or alkynyl group; and n is O, 1 or 2.

10 Claims, No Drawings

BENZISOXAZOLE COMPOUNDS USEFUL AS HERBICIDES

The present invention relates to novel substituted benzisoxazole derivatives, processes for their preparation, their use as herbicides and herbicidal compositions containing them.

European Patent No. 193700, GB2157679, GB2192878, GB2192879 and US4571255 describe certain benzisoxazolylphenyl ether derivatives which have herbicidal activity.

According to the present invention there is provided a compound of formula (I):

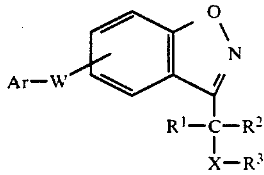

(I)

in which

Ar is an optionally substituted aryl or heterocyclic ring system;

$R^1$ and $R^2$ are independently selected from H, optionally substituted alkyl, alkenyl or alkynyl, halogen, $NR^aR^b$, or $R^1$ and $R^2$ together with the carbon to which they are attached form an optionally substituted alkenyl or cycloalkyl group;

$R^3$ is $CO_2R^4$, CN, $COR^4$, $CH_2OR^4$, $CH(OH)R^4$, $CH(OR^4)R^5$, $CH_2OSO_2R^4$, $CH_2OSO_3R^4$, $CH_2ONR^6R^7$, $CSNH_2$, $COSR^4$, $CSOR^4$, $CONHSO_2R^4$, $CONR^6R^7$, $CONHNR^6R^7$, $CONHN^+R^6R^7R^8$ $Y^-$, $CO_2^-M^+$ or $COON{=}CR^6R^7$;

$M^+$ is an agriculturally acceptable cation;

$Y^-$ is an agriculturally acceptable anion;

$R^4$, and $R^5$ are independently selected from H or an optionally substituted alkyl, aryl, alkenyl or alkynyl group;

$R^6$, $R^7$, $R^8$, $R^9$, $R^a$ and $R^b$ are independently selected from H or an optionally substituted alkyl, alkenyl, aryl or alkynyl group or any two of $R^6$, $R^7$, $R^9$, $R^a$ and $R^b$ together with the atom to which they are attached form a cycloalkyl or heterocyclic ring;

$R^6$ and $R^7$ may also be a heterocyclic ring;

W is O or $NR^{10}$ where is H or lower alkyl;

X is $(CH_2)_n$, $CH{=}CH$, $CH(OR^c)CH_2$, $COCH_2$;

where $R^c$ is H or an optionally substituted alkyl, aryl, alkynyl or alkynyl group; and n is O, 1 or 2.

As used herein the term "alkyl" includes straight or branched chains containing up to 10 carbon atoms preferably from 1 to 6 carbon atoms. The terms "alkenyl" and "alkynyl" refer to unsaturated straight or branched chains having from 2 to 10 and preferably from 2 to 6 carbon atoms. The term "cycloalkyl" includes rings containing from 3 to 9 carbon atoms, preferably from 3 to 6 carbon atoms. The term "alkoxy" includes straight or branched chains containing up to 10 carbon atoms preferably from 1 to 6 carbon atoms.

The term "lower" used in relation to alkyl, alkenyl or alkynyl groups means that the group contains up to 3 carbon atoms.

The term "haloalkyl" and "haloalkoxy" refer to alkyl and alkoxy groups respectively substituted by at least one halogen atom such as fluorine, chlorine or bromine. A particular haloalkyl group is trifluoromethyl. The term "aryl" includes phenyl and naphthyl. The term "heterocyclic" includes rings of up to 10 atoms, preferably up to 6 atoms up to 3 of which are selected from oxygen, nitrogen or sulphur. The term halogen includes fluorine, chlorine, bromine and iodine.

A suitable aryl ring system is phenyl.

Suitable heterocyclic ring systems for $R^6$, $R^7$ and Ar are rings of up to 10 atoms, up to 3 of which are selected from oxygen, nitrogen or sulphur, preferably aromatic ring systems such as pyridine and pyrazole.

Suitable optional substituents for the aryl or heterocyclic ring systems Ar and for the aryl groups $R^a$, $R^b$, $R^c$, $R^4$, $R^5$, $R^6$, $R^7$, $R^8$ and $R^9$ are up to 5 preferably up to 3 members selected from halogen (fluoro, chloro, bromo or iodo), lower alkyl, haloalkyl (for example $CF_3$), haloalkoxy (for example $OCF_3$), nitro, cyano, lower alkoxy (for example methoxy) or $S(O)_pR^d$ where p is 0, 1 or 2 and $R^d$ is alkyl (for example thiomethyl, sulphinylmethyl and sulphonylmethyl).

Preferred positions of substitution when the aryl ring Ar is a phenyl ring are the 2, 4 and 6 positions, particularly 2,4,6-tri- substituted rings with a trifluoromethyl group at the 4-position.

Examples of optional substituents for alkyl, alkenyl, alkynyl groups $R^a$, $R^b$, $R^c$, $R^1$, $R^2$, $R^4$, $R^5$, $R^6$, $R^7$, $R^8$ and $R^9$, include one or more groups selected from halo such as fluoro, chloro or bromo; nitro; cyano; aryl such as phenyl; $CO_2R^{11}$, $NHCOR^{11}$ or $NHCH_2CO_2R^{11}$ wherein $R^{11}$ is hydrogen, $C_{1-6}$ alkyl or an agriculturally acceptable cation; $C_{1-6}$ alkoxy; oxo; $S(O)_pR^3$ where p is 0, 1 or 2 and $R^d$ is alkyl (for example thiome , sulphinylmethyl and sulphonylmethyl); amino; mono- or di- $C_{1-6}$ alkylamino; $CONR^{12}R^{13}$ wherein $R^{12}$ and $R^{13}$ are independently selected from hydrogen, $C_{1-6}$ alkyl, $C_{2-6}$ alkenyl or $C_{2-6}$ alkynyl or $R^{12}$ and $R^{13}$ are joined together to form a heterocyclic ring having up to 7 ring atoms 3 of which may be selected from oxygen, nitrogen or sulphur. An example of a heterocyclic substituents is tetrahydrofuranyl.

Examples of agriculturally acceptable cations $M^+$ and $R^{11}$ include sodium, potassium or calcium ions, sulphonium or sulphoxonium ions or for example of formula $S^+(O)_qR^6R^7R^8$ where q is 0 or 1 and $R^6$, $R^7$ and are as hereinbefore defined, ammonium or tertiary ammonium ions of formula $N^+R^6R^7R^8R^9$ where $R^6$, $R^7$, $R^8$ and $R^9$ are as hereinbefore defined. Suitable substituents for the alkyl, alkenyl and alkynyl groups in these cations are hydroxy and phenyl. Suitably where any of $R^6$, $R^7$, $R^8$ and $R^9$ in the cations are optionally substituted alkyl, they contain from 1 to 4 carbon atoms.

Particular examples of $R^6$, $R^7$, $R^8$ and $R^9$ in these cations are hydrogen, ethyl, isopropyl, benzyl and 2-hydroxyethyl.

Examples of agriculturally acceptable anions for $Y^-$ are halides, tetrafluoroborate, mesylate and tosylate ions.

Suitable halo groups $R^1$, and $R^2$ include fluorine, chlorine and bromine.

Suitable heterocyclic rings formed from two of $R^a$, $R^b$, $R^6$, $R^7$, $R^8$ and $R^9$ and the atom to which they are attached are pyrrolidine, piperidine and morpholine.

Preferably $R^1$ is H.

Preferably $R^2$ is H or is $C_{1-3}$ alkyl, in particular methyl or ethyl.

Suitably $R^3$ is $CO_2R^4$, CN, $CH_2OR^4$, $CSNH_2$, $CONR^6R^7$, $CONHNR^6R^7$, $CONHN^+R^6R^7R^8$ $Y^-$, $COON{=}CR^6R^7$ or $CO_2^-M^+$.

Preferably $R^3$ is $CO_2R^4$, CN, $CONR^6R^7$ or $COON{=}CR^6R^7$, most preferably $R^3$ is $CO_2R^4$.

$R^4$ is preferably alkyl or substituted alkyl for example alkoxyalkyl or oxo substituted alkyl.

A preferred example of $R^4$ is $C_{1-6}$ alkyl, especially methyl.

Ar is preferably a group:

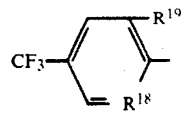

where $R^{18}$ is N, CH or $CR^{20}$ and $R^{19}$ and $R^{20}$ are independently selected from halogen, such as chlorine or fluorine. Preferably $R^{18}$ is $CR^{20}$ and most preferably one of $C^9$ and $C^{20}$ is chlorine and the other is fluorine.

Another group Ar is optionally substituted pyrazole, for example optionally substituted by Cl, $CF_3$ and $CH_3$.

W is preferably oxygen.

Preferably X is $(CH_2)n$ where n is zero or 1, especially zero.

The formula (I) given above is intended to include tautomeric forms of the structure drawn, as well as physically distinguishable modifications of the compounds which may arise, for example, from different ways in which the molecules are arranged in a crystal lattice, or from the inability of parts of the molecule to rotate freely in relation to other parts, or from geometrical isomerism, or from intra-molecular or inter-molecular hydrogen bonding, or otherwise.

Some of the compounds of the invention can exist in enantiomeric forms. The invention includes both individual enantiomers and mixtures of the two in all proportions.

Particular examples of compounds according to the invention are listed in Tables I, II and III. Characterising data for the compounds of Tables I, II and III are given in Table IV.

TABLE I

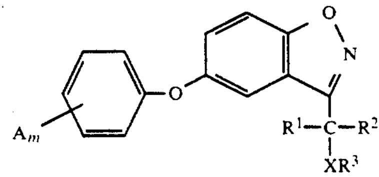

| Compound No | $A_m$ | $R^1$ | $R^2$ | $XR^3$ |
|---|---|---|---|---|
| 1 | 2-Cl.4-CF3.6-F | H | H | $CO_2H$ |
| 2 | 2-Cl.4-CF3.6-F | H | H | $CO_2Me$ |
| 3 | 2-Cl.4-CF3.6-F | Me | Me | $CO_2Me$ |
| 4 | 2-Cl.4-CF3.6-F | Br | H | $CO_2Me$ |
| 5 | 2-Cl.4-CF3.6-F | Me | H | $CO_2Me$ |
| 6 | 2-Cl.4-CF3.6-F | Et | H | $CO_2Me$ |
| 7 | 2-Cl,4-CF3.6-F | H | H | $CO_2Et$ |
| 8 | 2-Cl.4-CF3.6-F | Me | H | $CO_2Et$ |
| 9 | 2-Cl.4-CF3.6-F | Et | H | $CO_2Et$ |
| 10 | 2-Cl.4-CF3.6-F | H | H | $CO_2iPr$ |
| 11 | 2-Cl.4-CF3.6-F | H | H | $CO_2(CH_2)_2OMe$ |
| 12 | 2-Cl.4-CF3.6-F | H | H | $CO_2CH_2C{\equiv}CH$ |
| 13 | 2-Cl.4-CF3.6-F | H | H | $CO_2nBu$ |
| 14 | 2-Cl.4-CF3.6-F | Me | H | $CO_2H$ |
| 15 | 2-Cl,4-CF3.6-F | Me | H | $CO_2iPr$ |
| 16 | 2-Cl,4-CF3.6-F | Me | H | $CO_2nBu$ |
| 17 | 2-Cl.4-CF3.6-F | Me | H | $CO_2CH_2C{\equiv}CH$ |
| 18 | 2-Cl,4-CF3.6-F | Me | H | $CO_2(CH_2)_2OMe$ |
| 19 | 2-F,4-CF3.6-F | H | H | $CO_2Me$ |
| 20 | 2-F.4-CF3.6-F | H | H | $CO_2H$ |
| 21 | 2-F,4-CF3,6-F | H | H | $CO_2Et$ |
| 22 | 2-F,4-CF3,6-F | H | H | $CO_2iPr$ |
| 23 | 2-F,4-CF3,6-F | H | H | $CO_2nBu$ |
| 24 | 2-F,4-CF3,6-F | H | H | $CO_2(CH_2)_2OMe$ |
| 25 | 2-F,4-CF3,6-F | H | H | $CO_2CH_2C{\equiv}CH$ |
| 26 | 2-F,4-CF3,6-F | Me | H | $CO_2Me$ |
| 27 | 2-F,4-CF3,6-F | Me | H | $CO_2H$ |
| 28 | 2-F,4-CF3,6-F | Me | H | $CO_2Et$ |
| 29 | 2-F,4-CF3,6-F | Me | H | $CO_2iPr$ |
| 30 | 2-F,4-CF3,6-F | Me | H | $CO_2nBu$ |
| 31 | 2-F,4-CF3,6-F | Me | H | $CO_2(CH_2)_2OMe$ |
| 32 | 2-F,4-CF3,6-F | Me | H | $CO_2CH_2C{\equiv}CH$ |
| 33 | 2-CN,4-CF3 | H | H | $CO_2Me$ |
| 34 | 2-CN,4-CF3 | Me | H | $CO_2Me$ |
| 35 | 2-CN,4-CF3 | Me | Me | $CO_2Me$ |
| 36 | 2-CN,4-CF3 | H | H | $CO_2H$ |
| 37 | 2-CN,4-CF3 | H | H | $CO_2Et$ |
| 38 | 2-CN,4-CF3 | Me | H | $CO_2H$ |
| 39 | 2-CN,4-CF3 | Me | H | $CO_2Et$ |
| 40 | 2-Cl,4-CF3,6-F | H | H | $CO_2CH_2COMe$ |
| 41 | 2-Cl,4-CF3,6-F | Me | H | $CO_2CH_2COMe$ |
| 42 | 2-Cl,4-CF3 | H | H | $CO_2Me$ |
| 43 | 2-Cl,4-CF3 | H | H | $CO_2H$ |
| 44 | 2-Cl.4-CF3 | Me | H | $CO_2Me$ |
| 45 | 2-Cl,4-CF3 | Me | Me | $CO_2Me$ |

TABLE I-continued

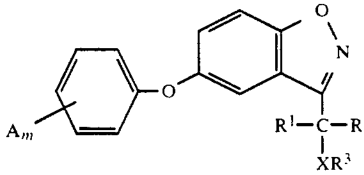

| Compound No | $A_m$ | $R^1$ | $R^2$ | $XR^3$ |
|---|---|---|---|---|
| 46 | 2-Cl,4-$CF_3$ | H | H | $CO_2Et$ |
| 47 | 2-Cl,4-$CF_3$ | Me | H | $CO_2H$ |
| 48 | 4-Cl,2,3,5,6-tetrafluoro | H | H | $CO_2Me$ |
| 49 | 4-Cl,2,3,5,6-tetrafluoro | Me | H | $CO_2Me$ |
| 50 | 4-Cl,2,3,5,6-tetrafluoro | H | H | $CO_2H$ |
| 51 | 4-Cl,2,3,5,6-tetrafluoro | H | H | $CO_2Et$ |
| 52 | 4-Cl,2,3,5,6-tetrafluoro | Me | H | $CO_2H$ |
| 53 | 4-Cl,2,3,5,6-tetrafluoro | Me | H | $CO_2Et$ |
| 60 | 2-$NO_2$,4-$CF_3$ | H | H | $CO_2Me$ |
| 61 | 2-$NO_2$,4-$CF_3$ | H | H | $CO_2H$ |
| 62 | 2-$NO_2$,4-$CF_3$ | Me | H | $CO_2Me$ |
| 63 | 2-Cl,4-$CF_3$,6-F | H | H | CONHMe |
| 64 | 2-Cl,4-$CF_3$,6-F | Me | H | CONHMe |
| 65 | 2-Cl,4-$CF_3$,6-OMe | Me | H | $CO_2Me$ |
| 66 | 2-Cl,4-$CF_3$,6-F | H | H | $CONMe_2$ |
| 67 | 2-Cl,4-$CF_3$,6-F | Me | H | $CONMe_2$ |
| 68 | 2-Cl,4-$CF_3$,6-F | H | H | $CONH_2$ |
| 69 | 2-Cl,4-$CF_3$,6-F | Me | H | $CONHNMe_2$ |
| 70 | 2-Cl,4-$CF_3$,6-F | H | H | $CONHNMe_2$ |
| 71 | 2-Cl,4-$SO_2Me$ | H | H | $CO_2Me$ |
| 72 | 2-Cl,4-$CF_3$,6-Cl | H | H | $CO_2Me$ |
| 73 | 2-Cl,4-$CF_3$,6-Cl | H | H | $CO_2H$ |
| 74 | 2-Cl,4-$CF_3$,6-Cl | Me | H | $CO_2Me$ |
| 75 | 2-Cl,4-$CF_3$,6-Cl | Me | H | $CO_2H$ |
| 76 | 2-Cl,4-$CF_3$,6-F | Cl | H | $CO_2Me$ |
| 77 | 2-F,4-CN,6-F | H | H | $CO_2Me$ |
| 78 | 2-F,4-CN,6-F | Me | H | $CO_2Me$ |
| 79 | 2-Cl,4-$CF_3$,6-F | Br | Br | $CO_2Me$ |
| 80 | 2-Cl,4-$CF_3$,6-OMe | H | H | $CO_2Me$ |
| 81 | 2-Cl,4-$CF_3$,6-F | H | H | $CONHN^+(CH_3)_3\ I^-$ |
| 82 | 2-Cl,4-$CF_3$,6-F | H | H | CN |
| 83 | 2-Cl,4-$CF_3$,6-F | H | H | $CH_2OH$ |
| 84 | 2-Cl,4-$CF_3$,6-F | H | H | 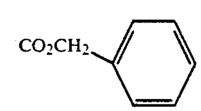 $CO_2CH_2$- |
| 85 | 2-Cl,4-$CF_3$,6-F | H | H | 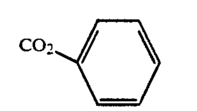 $CO_2$- |
| 86 | 2-Cl,4-$CF_3$,6-F | H | Me | $CONH_2$ |
| 87 | 2-Cl,4-$CF_3$,6-F | H | Me | CN |
| 88 | 2-Cl,4-$CF_3$,6-F | H | H | $CONH(CH_2)_2OCH_3$ |
| 89 | 2-Cl,4-Cl | H | H | $CO_2H$ |
| 90 | 2-Cl,4-$CF_3$,6-F | H | $CH_2CO_2Me$ | $CO_2Me$ |
| 91 | 2-Cl,4-$CF_3$,6-F | H | H | $CO_2N{=}C(CH_3)_2$ |
| 92 | 2-Cl,4-Cl | H | H | $CO_2Me$ |
| 93 | 2-Cl,4-$CF_3$,6-F | H | Br | $CO_2H$ |
| 94 | 2-Cl,4-$CF_3$,6-F | H | F | $CO_2Me$ |
| 95 | 2-Cl,4-Cl | H | H | $CO_2Et$ |
| 96 | 2-$CH_3$,4-Cl | H | H | $CO_2H$ |
| 97 | 2-Cl,4-Cl | H | Me | $CO_2Me$ |
| 98 | 2-$CH_3$,4-Cl | H | H | $CO_2Me$ |
| 99 | 2-Cl,4-$CF_3$,6-F | H | H | 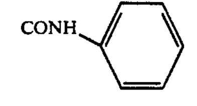 CONH- |

TABLE I-continued

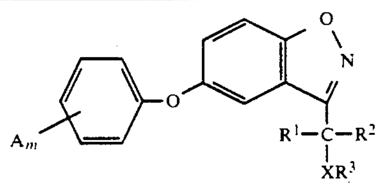

| Compound No | $A_m$ | $R^1$ | $R^2$ | $XR^3$ |
|---|---|---|---|---|
| 100 | 2-Cl,4-$CF_3$,6-F | H | $CH_2CN$ | $CO_2Me$ |
| 101 | 2-Cl,4-$CF_3$,6-F | H | Me | $CO_2N{=}C(CH_3)_2$ |
| 102 | 2-Cl,4-$CF_3$,6-F | H | Me | $CO_2^-Na^+$ |
| 103 | 2-Cl,4-$CF_3$,6-F | H | Me | $CO_2^-K^+$ |
| 104 | 2-Cl,4-$CF_3$,6-F | H | H | $CO_2^-Na^+$ |
| 105 | 2-Cl,4-$CF_3$,6-F | H | H | $CO_2^-K^+$ |
| 106 | 2-Cl,4-$CF_3$,6-F | H | H | $CO_2^-H_3N^+$iPr |
| 107 | 2-Cl,4-$CF_3$,6-F | H | H | $CO_2^-H_3N^+CH_2$-(phenyl) |
| 109 | 2-Cl,4-$CF_3$,6-F | H | H | CONH-(2-pyridyl) |
| 110 | 2-Cl,4-$CF_3$,6-F | H | H | CONH-(3-pyridyl) |
| 111 | 2-Cl,4-$CF_3$,6-F | H | H | CONH-(4-pyridyl) |
| 112 | 2-Cl,4-$CF_3$,6-F | H | $CH_2CH{=}CH_2$ | $CO_2Me$ |
| 113 | 2-Cl,4-$CF_3$,6-F | $CH_2CH{=}CH_2$ | $CH_2CH{=}CH_2$ | $CO_2Me$ |
| 114 | 2-Cl,4-$CF_3$,6-F | H | $CH_2C{\equiv}CH$ | $CO_2Me$ |
| 115 | 2-Cl,4-$CF_3$,6-F | $CH_2C{\equiv}CH$ | $CH_2C{\equiv}CH$ | $CO_2Me$ |
| 123 | 2-Cl,4-$CF_3$,6-F | H | H | $CSNH_2$ |

TABLE II

| Compound No | $R^1$ | $R^2$ | $XR^3$ |
|---|---|---|---|
| 54 | H | H | $CO_2Me$ |
| 55 | H | H | $CO_2H$ |
| 56 | Me | H | $CO_2Me$ |
| 57 | H | H | $CO_2Et$ |
| 58 | Me | H | $CO_2H$ |
| 59 | Me | H | $CO_2Et$ |
| 108 | Me | Me | $CO_2Et$ |

TABLE III

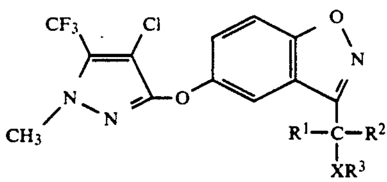

| Compound No | $R^1$ | $R^2$ | $XR^3$ |
|---|---|---|---|
| 116 | H | H | $CO_2H$ |
| 117 | H | H | $CO_2Me$ |
| 118 | H | H | $CO_2Et$ |
| 119 | H | H | $CO_2NH_2$ |
| 120 | H | Me | $CO_2H$ |
| 121 | H | Me | $CO_2Me$ |
| 122 | H | Me | $CO_2Et$ |

TABLE IV

| Compound No | Characterising Data |
|---|---|
| 1 | NMR δH($CDCl_3$): 4.0(s)2H; 5.5(broad s)1H; 7.1(d)1H; 7.25(dd)1H; 7.4(dd)1H; 7.5(s)1H; |

TABLE IV-continued

| Compound No | Characterising Data |
|---|---|
| | 7.6(s)1H. |
| 2 | NMR δH($CDCl_3$): 3.70(s)3H; 4.00(s)3H; 7.10(d)1H; 7.30(dd)1H; 7.40(dd)1H; 7.55(d)1H; 7.60(s)1H. |
| 3 | NMR δH($CDCl_3$): 1.70(s)6H; 3.60(s)3H; 7.10(d)1H; 7.20(dd)1H; 7.40(dd)1H; 7.50(d)1H; 7.60(s)1H. |
| 4 | NMR δH($CDCl_3$): 3.8(s)3H; 5.80(s)1H; 7.25(dd)1H; 7.45(m)2H; 7.60(d)1H; 7.70(broad s)1H. |
| 5 | NMR δH($CDCl_3$): 1.7(s)3H; 3.70(s)3H; 4.20(q)1H; 7.15(d)1H; 7.20(dd)1H; 7.40(dd)1H; 7.55(d)1H; 7.60(broad s)1H. |
| 6 | NMR δH($CDCl_3$): 1.00(t)3H; 2.10(m)1H; 2.30(m)1H; 3.70(s)3H; 4.00(t)1H; 7.20(m)2H; 7.45(dd)1H; 7.55(m)1H; 7.60(broad s)1H. |
| 7 | NMR δH($CDCl_3$): 1.20(t)3H; 4.00(s)2H; 4.15(q)2H; 7.10(d)1H; 7.30(dd)1H; 7.40(dd)1H; 7.55(d)1H; 7.60(broad s)1H. |
| 8 | NMR δH($CDCl_3$): 1.15(t)3H; 1.65(d)3H; 4.15(m)3H; 7.10(d)1H; 7.20(dd)1H; 7.40(dd)1H; 7.50(d)1H; 7.60(broad s)1H. |
| 9 | NMR δH($CDCl_3$): 1.00(t)3H; 1.15(t)3H; 2.05(m)1H; 2.30(m)1H; 4.00(t)1H; 4.10(q)2H; 7.20(m)2H; 7.40(dd)1H; 7.50(d)1H; 7.60(broad s)1H. |
| 10 | NMR δH($CDCl_3$): 1.15(d)6H; 3.95(s)2H; 5.05(sept)1H; 7.05(d)1H; 7.3(dd)1H; 7.4(dd)1H; 7.55(d)1H; 7.6(bs)1H. |
| 11 | NMR δH($CDCl_3$): 3.3(s)3H; 3.55(m)2H; 4.0(s)2H; 4.3(m)2H; 7.1(d)1H; 7.25(dd)1H; 7.4(dd)1H; 7.55(d)1H; 7.6(bs)1H. |
| 12 | NMR δH($CDCl_3$): 2.5(t)1H; 4.05(s)2H; 4.7(d)2H; 7.1(d)1H; 7.3(dd)1H; 7.45(dd)1H; 7.55(d)1H; 7.65(bs)1H. |
| 13 | NMR δH($CDCl_3$): 0.9(t)3H; 1.3(sext)2H; 1.55(m)2H; 4.0(s)2H; 4.1(t)2H; 7.1(d)1H; 7.3(dd)1H; 7.4(dd)1H; 7.55(d)1H; 7.6(bs)1H. |
| 14 | NMR δH($CDCl_3$): 1.7(d)3H; 4.25(q)1H; 7.25(m)2H; 7.4(dd)1H; 7.5(d)1H; 7.6(bs)1H. |
| 15 | NMR δH($CDCl_3$): 1.05(d)3H; 1.15(d)3H; 1.65(d)3H; 4.15(q)1H; 5.0(sept)1H; 7.1(d)1H; 7.25(dd)1H; 7.4(dd)1H; 7.55(d)1H; 7.6(bs)1H. |
| 16 | NMR δH($CDCl_3$): 0.85(t)3H; 1.2(sext)2H; 1.5(quin)2H; 1.7(d)3H; 4.1(t)2H; 4.2(q)1H; 7.15(d)1H; 7.2(dd)1H; 7.4(dd)1H; 7.5(d)1H; 7.6(bs)1H. |
| 17 | NMR δH($CDCl_3$): 1.7(d)3H; 2.4(t)1H; 4.25(q)1H; 4.7(m)2H; 7.2(m)2H; 7.4(dd)1H; 7.5(d)1H; 7.6(bs)1H. |
| 18 | NMR δH($CDCl_3$): 1.7(d)3H; 3.25(s)3H; 3.5(t)2H; 4.25(m)3H; 7.2(m)2H; 7.4(dd)1H; 7.5(d)1H; 7.6(bs)1H. |
| 19 | NMR δH($CDCl_3$): 3.7(s)3H; 4.0(s)2H; 7.2(d)1H; 7.3(m)3H; 7.55(d)1H. |
| 20 | NMR δH($CDCl_3$): 4.05(s)2H; 7.2(d)1H; 7.3(m)3H; 7.55(d)1H. |
| 21 | NMR δH($CDCl_3$): 1.2(t)3H; 4.0(s)2H; 4.15(q)2H; 7.15(d)1H; 7.35(m)3H; 7.55(d)1H. |
| 22 | NMR δH($CDCl_3$): 1.2(d)6H; 3.95(s)2H; 5.05(sept)1H; 7.15(d)1H; 7.35(m)3H; 7.55(d)1H. |
| 23 | NMR δH($CDCl_3$): 0.9(t)3H; 1.3(m)2H; 1.55(m)2H; 4.0(s)2H; 4.1(t)2H; 7.2(d)1H; 7.3(m)3H; 7.55(d)1H. |
| 24 | NMR δH($CDCl_3$): 3.3(s)3H; 3.55(m)2H; 4.0(s)2H; 4.3(m)2H; 7.2(d)1H; 7.3(m)3H; 7.55(d)1H. |
| 25 | NMR δH($CDCl_3$): 2.45(t)1H; 4.05(s)2H; 4.7(d)2H; 7.2(d)1H; 7.35(m)3H; 7.55(d)1H. |
| 26 | NMR δH($CDCl_3$): 1.7(d)3H; 3.7(s)3H; 4.2(q)1H; 7.3(m)4H; 7.55(d)1H. |
| 27 | NMR δH($CDCl_3$): 1.7(d)3H; 4.25(q)1H; 7.3(m)4H; 7.55(m)1H. |
| 28 | NMR δH($CDCl_3$): 1.15(t)3H; 1.7(d)3H; 4.2(m)3H; 7.2(d)1H; 7.4(m)3H; 7.55(d)1H. |
| 29 | NMR δH($CDCl_3$): 1.1(d)3H; 1.15(d)3H; 1.7(d)3H; 4.15(m)1H; 5.0(m)1H; 7.2(d)1H; 7.3(m)3H; 7.55(d)1H. |
| 30 | NMR δH($CDCl_3$): 0.8(t)3H; 1.2(sext)2H; |

TABLE IV-continued

| Compound No | Characterising Data |
|---|---|
| | 1.5(quin)2H; 1.7(d)3H; 4.1(t)2H; 4.2(q)1H; 7.3(m)4H; 7.55(d)1H. |
| 31 | NMR δH($CDCl_3$): 1.7(d)3H; 3.25(s)3H; 3.5(t)2H; 4.25(m)3H; 7.3(m)4H; 7.55(d)1H. |
| 32 | NMR δH($CDCl_3$): 1.7(d)3H; 2.4(t)1H; 4.25(q)1H; 4.7(m)2H; 7.25(d)1H; 7.3(m)3H; 7.55(m)1H. |
| 33 | NMR δH($CDCl_3$): 3.75(s)3H; 4.05(s)2H; 6.7(d)1H; 7.35(dd)1H; 7.5(d)1H; 7.7(m)2H; 7.95(d)1H. |
| 34 | NMR δH($CDCl_3$): 1.7(d)3H; 3.7(s)3H; 4.3(q)1H; 6.9(d)1H; 7.35(dd)1H; 7.55(d)1H; 7.7(m)2H; 8.0(d)1H. |
| 35 | NMR δH($CDCl_3$): 1.8(s)6H; 3.7(s)3H; 6.85(d)1H; 7.3(dd)1H; 7.4(d)1H; 7.7(m)2H; 8.0(d)1H. |
| 36 | NMR δH($CDCl_3$): 4.1(s)2H; 6.1(bs)1H; 6.9(d)1H; 7.4(dd)1H; 7.5(d)1H; 7.7(m)2H; 7.9(d)1H. |
| 37 | NMR δH($CDDl_3$): 1.25(t)3H; 4.0(s)2H; 4.2(q)2H; 6.9(d)1H; 7.35(dd)1H; 7.5(d)1H; 7.7(m)2H; 8.0(bs)1H. |
| 38 | NMR δH($CDCl_3$): 1.75(d)3H; 4.3(q)1H; 6.0(bs)1H; 6.85(d)1H; 7.35(dd)1H; 7.5(d)1H; 7.7(m)2H; 7.95(d)1H. |
| 39 | NMR δH($CDCl_3$): 1.2(t)3H; 1.7(d)3H; 4.2(m)3H; 6.85(d)1H; 7.35(dd)1H; 7.55(d)1H; 7.7(m)2H; 7.95(d)1H. |
| 40 | NMR δH($CDCl_3$): 2.1(s)3H; 4.1(s)2H; 4.7(s)2H; 7.15(d)1H; 7.3(dd)1H; 7.4(dd)1H; 7.55(d)1H; 7.6(bs)1H. |
| 41 | NMR δH($CDCl_3$): 1.75(d)3H; 2.05(s)3H; 4.3(q)1H; 4.65(s)2H; 7.25(m)2H; 7.4(dd)1H; 7.55(d)1H; 7.6(bs)1H. |
| 42 | NMR δH($CDCl_3$): 3.7(s)3H; 4.0(s)2H; 6.9(d)1H; 7.3(d)1H; 7.3(m)2H; 7.45(dd)1H; 7.6(d)1H; 7.8(d)1H. |
| 43 | NMR δH($CDCl_3$): 4.05(s)2H; 6.4(bs)1H; 6.9(d)1H; 7.3(m)2H; 7.45(dd)1H; 7.6(dd)1H; 7.75(d)1H. |
| 44 | NMR δH($CDCl_3$): 1.7(d)3H; 3.7(s)3H; 4.25(q)1H; 6.9(d)1H; 7.25(d)1H; 7.4(m)2H; 7.6(d)1H; 7.8(d)1H. |
| 45 | NMR δH($CDCl_3$): 1.75(s)6H; 3.75(s)3H; 6.85(d)1H; 7.25(m)2H; 7.45(dd)1H; 7.6(d)1H; 7.8(d)1H. |
| 46 | NMR δH($CDCl_3$): 1.25(t)3H; 4.0(s)2H; 4.2(q)2H; 6.9(d)1H; 7.3(m)2H; 7.45(dd)1H; 7.55(dd)1H; 7.8(d)1H. |
| 47 | NMR δH($CDCl_3$): 1.7(d)3H; 4.25(q)1H; 6.9(d)1H; 7.3(dd)1H; 7.4(m)2H; 7.6(d)1H; 7.75(d)1H. |
| 48 | NMR δH($CDCl_3$): 3.7(s)3H; 4.0(s)2H; 7.2(d)1H; 7.3(dd)1H; 7.55(d)1H. |
| 49 | NMR δH($CDCl_3$): 1.7(d)3H; 3.7(s)3H; 4.2(q)1H; 7.3(m)2H; 7.55(d)1H. |
| 50 | NMR δH($CDCl_3$): 4.0(s)2H; 6.5(bs)1H; 7.2(d)1H; 7.35(dd)1H; 7.55(d)1H. |
| 51 | NMR δH($CDCl_3$): 1.2(t)3H; 4.0(s)2H; 4.2(q)2H; 7.2(d)1H; 7.3(dd)1H; 7.6(d)1H. |
| 52 | NMR δH($CDCl_3$): 1.7(d)3H; 4.3(q)1H; 7.3(m)2H; 7.6(d)1H; 8.6(bs)1H. |
| 53 | NMR δH($CDCl_3$): 1.2(t)3H; 1.7(d)3H; 4.2(m)3H; 7.3(m)2H; 7.55(d)1H. |
| 54 | NMR δH($CDCl_3$): 3.7(s)3H; 4.0(s)2H; 7.4(dd)1H; 7.55(d)1H; 7.65(d)1H; 8.0(d)1H; 8.25(d)1H. |
| 55 | NMR δH($CDCl_3$): 4.05(s)2H; 7.4(dd)1H; 7.5(d)1H; 7.65(d)1H; 8.0(d)1H; 8.2(bs)1H. |
| 56 | NMR δH($CDCl_3$): 1.7(d)3H; 3.7(s)3H; 4.3(q)1H; 7.4(dd)1H; 7.55(d)1H; 7.65(d)1H; 8.0(d)1H; 8.25(bs)1H. |
| 57 | NMR δH($CDCl_3$): 1.2(t)3H; 4.0(s)3H; 4.2(q)2H; 7.4(dd)1H; 7.55(d)1H; 7.65(d)1H; 8.0(d)1H; 8.25(bs)1H. |
| 58 | NMR δH($CDCl_3$): 1.7(d)3H; 4.3(q)1H; 6.2(bs)1H; 7.35(dd)1H; 7.55(d)1H; 7.65(d)1H; 8.0(d)1H; 8.2(d)1H. |
| 59 | NMR δH($CDCl_3$): 1.2(t)3H; 1.7(d)3H; 4.2(m)3H; 7.4(dd)1H; 7.55(d)1H; 7.65(d)1H; |

TABLE IV-continued

| Compound No | Characterising Data |
|---|---|
| | 8.0(d)1H; 8.2(d)1H. |
| 60 | NMR $\delta H(CDCl_3)$: 3.7(s)3H; 4.0(s)2H; 7.0(d)1H; 7.35(dd)1H; 7.5(d)1H; 7.65(d)1H; 7.7(dd)1H; 8.25(d)1H. |
| 61 | NMR $\delta H(CDCl_3)$: 4.1(s)2H; 7.0(d)1H; 7.35(dd)1H; 7.45(d)1H; 7.65(d)1H; 7.7(dd)1H; 8.25(d)1H. |
| 62 | NMR $\delta H(CDCl_3)$: 1.7(d)3H; 3.7(s)3H; 4.3(q)1H; 7.0(d)1H; 7.35(dd)1H; 7.5(d)1H; 7.65(d)1H; 7.7(dd)1H; 8.25(d)1H. |
| 63 | NMR $\delta H(CDCl_3)$: 2.8(d)3H; 3.9(s)2H; 6.2(bs)1H; 7.1(d)1H; 7.35(dd)1H; 7.45(dd)1H; 7.55(d)1H; 7.65(bs)1H. |
| 64 | NMR $\delta H(CDCl_3)$: 1.7(d)3H; 2.7(d)3H; 4.1(q)1H; 6.1(bs)1H; 7.25(m)2H; 7.4(dd)1H; 7.55(m)1H; 7.6(bs)1H. |
| 65 | NMR $\delta H(CDCl_3)$: 1.7(d)3H; 3.65(s)3H; 3.85(s)3H; 4.1(q)1H; 7.05(d)1H; 7.2(m)2H; 7.4(bs)1H; 7.5(d)1H. |
| 66 | NMR $\delta H(CDCl_3)$: 2.95(s)3H; 3.1(s)3H; 4.0(s)2H; 7.25(m)2H; 7.4(dd)1H; 7.5(d)1H; 7.6(bs)1H. |
| 67 | NMR $\delta H(CDCl_3)$: 1.6(d)3H; 2.9(s)3H; 3.05(s)3H; 4.5(q)1H; 7.2(dd)1H; 7.4(m)2H; 7.5(d)1H; 7.6(bs)1H. |
| 68 | NMR $\delta H(CDCl_3)$: 3.9(s)2H; 5.8(bs)1H; 6.2(bs)1H; 7.1(d)1H; 7.35(dd)1H; 7.45(dd)1H; 7.55(d)1H; 7.65(bs)1H. |
| 69 | NMR $\delta H(CDCl_3)$: 1.6(d)+1.65(d)3H; 2.5(s)6H; 4.1(q)+4.85(q)1H; 6.7(bs)1H; 7.25(m)2H; 7.4(dd)1H; 7.5(m)1H; 7.6(bs)1H. |
| 70 | NMR $\delta H(CDCl_3)$: 2.52(s)+2.54(s)6H; 3.8(s)+4.15(s)2H; 6.5(bs)1H; 7.1-7.6(m)5H. |
| 71 | NMR $\delta H(CDCl_3)$: 3.1(s)3H; 3.8(s)3H; 4.0(s)2H; 6.9(d)1H; 7.15(dd)1H; 7.2(d)1H; 7.3(d)1H; 7.8(dd)1H; 8.05(d)1H. |
| 72 | NMR $\delta H(CDCl_3)$: 3.7(s)3H; 4.0(s)2H; 6.95(d)1H; 7.2(dd)1H; 7.6(d)1H; 7.8(s)2H. |
| 73 | NMR $\delta H(CDCl_3)$: 4.0(s)2H; 6.95(d)1H; 7.2(dd)1H; 7.55(d)1H; 7.7(s)2H. |
| 74 | NMR $\delta H(CDCl_3)$: 1.7(d)3H; 3.7(s)3H; 4.1(q)1H; 7.0(d)1H; 7.2(dd)1H; 7.55(d)1H; 7.7(s)2H. |
| 75 | NMR $\delta H(CDCl_3)$: 1.7(d)3H; 4.25(q)1H; 7.05(d)1H; 7.15(dd)1H; 7.55(d)1H; 7.7(s)2H. |
| 76 | NMR $\delta H(CDCl_3)$: 3.8(s)3H; 5.8(s)1H; 7.3(m)1H; 7.35(d)1H; 7.45(dd)1H; 7.6(d)1H; 7.65(bs)1H. |
| 77 | NMR $\delta H(CDCl_3)$: 3.7(s)3H; 4.0(s)2H; 7.2(d)1H; 7.3(dd)1H; 7.4(d)2H; 7.6(d)1H. |
| 78 | NMR $\delta H(CDCl_3)$: 1.7(d)3H; 3.7(s)3H; 4.2(q)1H; 7.25(m)2H; 7.4(d)2H; 7.55(d)1H. |
| 79 | NMR $\delta H(CDCl_3)$: 3.95(s)3H; 7.25(dd)1H; 7.35(d)1H; 7.45(dd)1H; 7.55(d)1H; 7.63(bs)1H. |
| 80 | NMR $\delta H(CDCl_3)$: 3.7(s)3H; 3.8(s)3H; 4.0(s)2H; 7.0(d)1H; 7.15(d)1H; 7.2(dd)1H; 7.4(s)1H; 7.5(d)1H. |
| 81 | NMR $\delta H(CDCl_3)$: 3.9(s)9H; 4.3(s)2H; 7.3(m)2H; 7.45(dd)1H; 7.6(bs)1H. |
| 82 | NMR $\delta H(CDCl_3)$: 4.05(s)2H; 7.15(d)1H; 7.35(dd)1H; 7.45(dd)1H; 7.6(d+bs)2H. |
| 83 | NMR $\delta H(CDCl_3)$: 2.2(bt)1H; 3.15(t)2H; 4.1(q)2H; 7.05(d)1H; 7.3(dd)1H; 7.4(dd)1H; 7.55(d)1H; 7.6(bs)1H. |
| 84 | NMR $\delta H(CDCl_3)$: 4.0(s)2H; 5.15(s)2H; 7.1(d)1H; 7.3(m)6H; 7.4(dd)1H; 7.55(d)1H; 7.6(bs)1H. |
| 85 | NMR $\delta H(CDCl_3)$: 4.2(s)2H; 6.8(d)1H; 6.9(t)1H; 7.0(d)1H; 7.15(d)1H; 7.2-7.4(m)4H; 7.6(m)2H. |
| 86 | NMR $\delta H(CDCl_3)$: 1.7(d)3H; 4.1(q)1H; 5.5(bs)1H; 5.95(bs)1H; 7.25(m)2H; 7.4(dd)1H; 7.55(d)1H; 7.6(bs)1H. |
| 87 | NMR $\delta H(CDCl_3)$: 1.85(d)3H; 4.35(q)1H; 7.3(m)2H; 7.45(dd)1H; 7.6(m)2H. |
| 88 | NMR $\delta H(CDCl_3)$: 3.3(s)3H; 3.4(2×s)4H; 3.85(s)2H; 6.4(bs)1H; 7.15(d)1H; 7.3(dd)1H; 7.4(dd)1H; 7.55(d)1H; 7.6(bs)1H. |
| 89 | NMR $\delta H(CDCl_3)$: 4.0(s)2H; 6.0(bs)1H; 6.9(d)1H; 7.15(m)1H; 7.2(m)1H; 7.3(d)1H; 7.45(d)1H; 7.6(d)1H. |
| 90 | NMR $\delta H(CDCl_3)$: 3.05(dd)1H; 3.4(dd)1H; 3.7(2×s)6H; 4.55(m)1H; 7.15(d)1H; 7.3(dd)1H; 7.45(dd)1H; 7.55(d)1H; 7.65(bs)1H. |
| 91 | NMR $\delta H(CDCl_3)$: 1.85(s)3H; 2.0(s)3H; 4.1(s)2H; 7.1(d)1H; 7.3(dd)1H; 7.4(dd)1H; 7.55(d)1H; 7.6(bs)1H. |
| 92 | NMR $\delta H(CDCl_3)$: 3.7(s)3H; 4.0(s)2H; 6.9(d)1H; 7.2(m)3H; 7.5(d)1H; 7.6(d)1H. |
| 93 | NMR $\delta H(CDCl_3)$: 5.8(bs)1H; 6.45(bs)1H; 7.25(dd)1H; 7.55(d)1H; 7.6(bs)1H; 7.9(m)2H. |
| 94 | NMR $\delta H(CDCl_3)$: 3.8(s)3H; 6.2-6.4(d)1H; 7.2(d)1H; 7.35(dd)1H; 7.45(dd)1H; 7.6(bs+d)2H. |
| 95 | NMR $\delta H(CDCl_3)$: 1.25(t)3H; 3.95(s)2H; 4.2(q)2H; 6.9(d)1H; 7.25(dodd)3H; 7.5(d)1H; 7.6(d)1H. |
| 96 | NMR $\delta H(CDCl_3)$: 2.25(s)3H; 4.05(s)2H; 6.75(d)1H; 7.1(m)2H; 7.25(m)2H; 7.55(d)1H. |
| 97 | NMR $\delta H(CDCl_3)$: 1.7(d)3H; 3.7(s)3H; 4.2(q)1H; 6.85(d)1H; 7.2(m)3H; 7.5(d)1H; 7.55(d)1H. |
| 98 | NMR $\delta H(CDCl_3)$: 2.25(s)3H; 3.7(s)3H; 4.0(s)2H; 6.8(d)1H; 7.1(m)2H; 7.25(m)2H; 7.55(m)1H. |
| 99 | NMR $\delta H(CDCl_3)$: 4.05(s)2H; 7.1(m)2H; 7.3-7.35(m)4H; 7.4(dd)1H; 7.55(d)1H; 7.6(bs+d)2H; 8.05(bs)1H. |
| 100 | NMR $\delta H(CDCl_3)$: 3.25(dodd)2H; 3.75(s)3H; 4.4(t)1H; 7.1(d)1H; 7.3(dd)1H; 7.45(dd)1H; 7.6(d)1H; 7.65(s)1H. |
| 101 | NMR $\delta H(CDCl_3)$: 1.75(d+s)6H; 2.0(s)3H; 4.35(q)1H; 7.25(m)2H; 7.4(dd)1H; 7.55(d)1H; 7.6(bs)1H. |
| 102 | NMR $\delta H(DMSO+CDCl_3)$: 1.55(d)3H; 3.95(q)1H; 7.05(dd)1H; 7.4(d)1H; 7.45(dd)1H; 7.5(d)1H; 7.65(bs)1H. |
| 103 | NMR $\delta H(DMSO)$: 1.35(d)3H; 3.6(q)1H; 7.25(dd)1H; 7.45(d)1H; 7.6(d)1H; 8.0(m)2H. |
| 104 | NMR $\delta H(DMSO)$: 3.4(s)2H; 7.2-7.3(d+dd)2H; 7.6(d)1H; 7.95(m)2H. |
| 105 | NMR $\delta H(DMSO)$: 3.35(s)2H; 7.25(m)2H; 7.55(d)1H; 7.95(m)2H. |
| 106 | NMR $\delta H(CDCl_3)$: δ0.95(d)6H; 3.05(m)1H; 3.75(s)2H; 6.5(bs)(NH$_3$); 7.1(d)1H; 7.2(dd)1H; 7.4(dd)1H; 7.45(d)1H; 7.6(bs)1H. |
| 107 | NMR $\delta H(CDCl_3)$: 3.5(s)2H; 3.7(s)2H; 5.3(bs)3H; 7.1-7.2(m)7H; 7.45(dd)1H; 7.5(d)1H; 7.55(bs)1H. |
| 108 | NMR $\delta H(CDCl_3)$: 1.15(t)3H; 1.75(s)6H; 4.15(q)2H; 7.35(dd)1H; 7.45(d)1H; 7.65(d)1H; 8.0(d)1H; 8.2(m)1H. |
| 109 | NMR $\delta H(CDCl_3)$: 4.1(s)2H; 7.05(dd)1H; 7.15(d)1H; 7.3(dd)1H; 7.4(dd)1H; 7.6(m)2H; 7.7(m)1H; 8.15(d)1H; 8.3(d)1H; 8.7(bs)1H. |
| 110 | NMR $\delta H(DMSO+CDCl_3)$: 4.05(s)2H; 7.25(dd)1H; 7.3(m)2H; 7.6-7.75(m)3H; 7.95(dd)1H; 8.25(d)1H; 8.65(d)1H; 10.55(bs)1H. |
| 111 | NMR $\delta H(DMSO+CDCl_3)$: 4.1(s)2H; 7.25(m)2H; 7.45(dd)1H; 7.5-7.6(m)3H; 7.65(bs)1H; 8.45(d)2H; 10.5(bs)1H. |
| 112 | NMR $\delta H(CDCl_3)$: 2.8(m)1H; 3.0(m)1H; 3.7(s)3H; 4.2(t)1H; 5.1(m)2H; 5.8(m)1H; 7.2(s)1H; 7.25(s)1H; 7.45(dd)1H; 7.5(d)1H; 7.6(s)1H. |
| 113 | NMR $\delta H(CDCl_3)$: 2.9(m)4H; 3.6(s)3H; 5.05(d+s)4H; 5.6(m)2H; 7.0(d)1H; 7.2(dd)1H; 7.4(dd)1H; 7.55(d)1H; 7.6(s)1H. |
| 114 | NMR $\delta H(CDCl_3)$: 2.0(t)1H; 3.05(qodd)2H; 3.7(s)3H; 4.3(t)1H; 7.15(d)1H; 7.25(dd)1H; 7.35(dd)1H; 7.45(d)1H; 7.65(s)1H. |
| 115 | NMR $\delta H(CDCl_3)$: 2.0(t)2H; 3.3(d)4H; 3.7(s)3H; 7.1(d)1H; 7.2(dd)1H; 7.4(dd)1H; 7.55(d)1H; 7.6(s)1H. |
| 116 | NMR $\delta H(DMSO)$: 3.8(s)3H; 4.05(s)2H; 7.45(dd)1H; 7.6(d)1H; 7.7(d)1H; 12.85(b)1H. |
| 117 | NMR $\delta H(CDCl_3)$: 3.75(s)3H; 3.9(s)3H; 4.05(s)2H; 7.4(dd)1H; 7.45(s)1H; 7.55(dd)1H. |
| 118 | NMR $\delta H(CDCl_3)$: 1.25(t)3H; 3.85(s)3H; |

TABLE IV-continued

| Compound No | Characterising Data |
|---|---|
| | 4.0(s)2H; 4.2(q)2H; 7.4(d)1H; 7.45(s)1H; 7.55(d)1H. |
| 119 | NMR δH(CDCl3): 3.9(s)3H; 3.95(s)2H; 5.65(b)1H; 6.25(b)1H; 7.4(dd)1H; 7.45(d)1H; 7.6(d)1H. |
| 120 | NMR δH(DMSO): 1.7(d)3H; 4.0(s)3H; 4.45(q)1H; 7.65(dd)1H; 7.75(d)1H; 7.9(d)1H; 13.1(b)1H. |
| 121 | NMR δH(CDCl3): 1.75(d)3H; 3.7(s)3H; 3.9(s)3H; 4.25(q)1H; 7.4(dd)1H; 7.5(d)1H; 7.55(d)1H. |
| 122 | NMR δH(CDCl3): 1.2(t)3H; 1.7(d)3H; 3.9(s)3H; 4.15(q)2H; 4.2(q)1H; 7.4(dd)1H; 7.5(d)1H; 7.55(d)1H. |
| 123 | NMR δH(DMSO+CDCl3): 4.2(s)2H; 7.25(dd)1H; 7.4(d)1H; 7.6(d)1H; 7.65(dd)1H; 7.75(bs)1H; 9.45(bs)1H; 9.6(bs)1H. |

Compounds of formula (I) may be prepared by reacting a compound of formula (II):

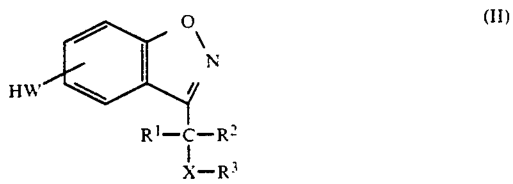

wherein W, X, $R^1$, $R^2$ and $R^3$ are as defined in relation to formula (I) with a compound of formula (III):

Ar—Z (III)

wherein Ar is as defined in relation to formula (I) and Z is a leaving group, optionally in the presence of a base.

Suitable leaving groups Z include halogen, such as fluorine, bromine and chlorine, and sulphonates such as methanesulphonate and p-toluenesulphonate.

Suitable bases for use in the reaction include bases such as sodium hydride, and alkali metal carbonates and hydroxides.

The reaction is preferably carried out in an organic solvent such as dimethylformamide, dimethylsulphoxide, a lower alkanol, or a lower ketone. Moderate temperatures, for example of from 10° C. to 200° C. are suitably employed Conveniently the reaction is carried out at 50° C. to 150° C.

When compounds of formula (III) contain an aryl or heterocyclic ring system substituted by more than one group which is capable of acting as a leaving group, the reaction product may consist of a mixture of regioisomers. These isomers may be inseparable and mixture composition is analysed by $^1H$ NMR and $^{19}F$ NMR, when appropriate.

Compounds of formula (II) can be prepared from a dihydroxycoumarin e.g. according to the procedure described in Phytochemistry, 1971, 10,539–544.

Dihydroxycoumarins are known compounds and compounds of formula (III) are known compounds or may be prepared from known compounds by conventional methods.

An alternative method of preparing compounds of formula (I) where n is 0, $R^1$ and $R^2$ are H and $R^3$ is $CO_2H$ involves the reaction of compounds of formula (IV):

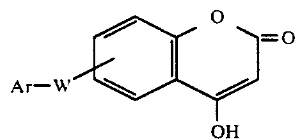

where Ar and W are as defined in relation to formula (I), with hydroxylamine hydrochloride in the presence of a base.

Suitable bases for use in the reaction include bases such as alkali metal hydroxides, carbonates and alkoxides.

The reaction is preferably carried out in an organic solvent such as dimethylformamide, dimethyl sulphoxide or a lower alkanol. Moderate temperatures, for example from 10° C. to 120° C. are suitably employed. Conveniently the reaction is carried out at 20° C. to 110° C.

Compounds of formula (IV) are novel and as such form a further aspect of the invention.

Compounds of formula (IV) may be prepared by the reaction of a compound of formula (V):

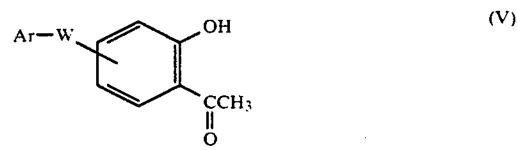

with a suitable derivative of carbonic acid, for example ethyl chloroformate or diethyl carbonate, in the presence of a base.

Suitable bases for use in the reaction include bases such as alkali metals, alkali metal hydrides or alkoxides.

The reaction may be carried out in either the presence or absence of solvent. If a solvent is employed, suitable solvents are for example toluene, dimethylformamide, dimethyl sulphoxide or terahydrofaran. Moderate temperatures, for example from 50° C. to 150° C. are suitably employed. Conveniently the reaction is carried out at 70° C. to 120° C.

Compounds of formula (V) are novel and as such form a further aspect of the invention.

Compounds of formula (V) may be prepared from compounds of formula (VI):

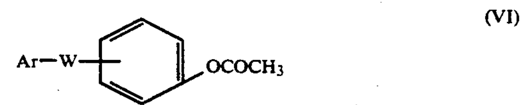

by a Lewis acid catalysed Fries rearrangement.

Aluminium trichloride is a suitable catalyst. The reaction may be carried out in the absence of solvent. Higher temperatures, for example 100° C. to 200° C. are suitably employed.

Compounds of formula (VI) are readily prepared by literature methods from the corresponding phenols of formula (VII):

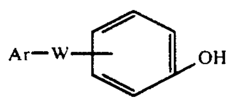

The phenols (VII) may in turn be prepared from either the acetophenones of formula (VIII):

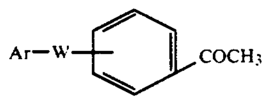

or by a Baeyer Villager oxidation or from the nitro compounds of formula (IX):

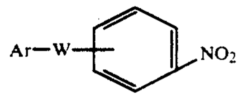

via standard functional group intercoversions.

Compounds of formula (VIII) and (IX) may be prepared by the reaction of a compound of formula (X):

Ar—WH (X)

wherein Ar and W are as defined in relation to formula (I) and a compound of formula (XI):

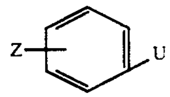

wherein U is $COCH_3$ or $NO_2$ and Z is a leaving group as defined for formula (III), optionally in the presence of a base.

Suitable bases for the reaction include bases such as sodium hydride, alkali metal carbonates and hydroxides, and organic nitrogen bases, for example triethylamine, 4-dimethylamino pyridine or 4-pyrolidinopyridine.

The reaction is preferably carried out in an organic solvent such as dimethylformamide, dimethyl sulphoxide a lower alkanol, a chlorinated solvent or a lower ketone. Moderate temperatures, for example 10° C. to 200° C. are suitably employed. Conveniently the reaction is carried out at 50° C. to 180° C.

Alternatively compounds of formula (V) may be prepared from amines of formula (XII):

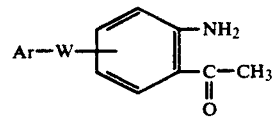

where Ar and W are defined in relation to formula (I), by diazotisation followed by decomposition of the diazonium salt.

Suitable reagents for diazotisation are sodium nitrite in aqueous acid, for example hydrochloric acid at a temperature of −10° to 10° C. The diazonium compound may be precipitated as the tetrafluoroborate salt. The tetrafluoroborate salt of the diazonium compound may be decomposed by an alkali carbonate, e.g. potassium carbonate under acidic conditions, e.g. neat TFA, at elevated temperatures, for example 30°–100° C., followed by an aqueous work up. Alternatively the tetrafluoroborate salt of the diazonium compound may be decomposed under aqueous conditions by copper salts, e.g. a mixture of cupric nitrate and cuprous oxide, at elevated temperatures, for example 30°–100° C.

The compounds of formula (XII) may be prepared by reduction of nitro compounds of formula (XIII):

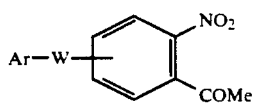

wherein Ar and W are as defined in relation to formula (I).

Typically the nitro compound is reduced in a solution in an organic solvent, for example ethanol, by hydrogen or a source of hydrogen, for example hydrazine, using a catalyst, for example Raney nickel at moderate temperatures, for example 20° to 120° C. Alternatively, a solution of the nitro compound (XIII) in an organic solvent, for example ethanol or acetone, may be reduced by an aqueous solution of titanium trichloride initially at low temperatures, for example −25° to 10° C.

Compounds of formula (XIII) may be prepared from the reaction of compounds of formula (X) with compounds of formula (XIV):

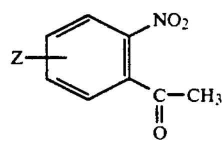

where Z is a leaving group as defined in formula (III), optionally in the presence of base.

Suitable bases for the reaction include bases such as sodium hydride, alkali metal carbonates and hydroxides, and organic nitrogen bases, for example triethylamine, 4-dimethylaminopyridine or 4-pyrrolopyridine.

The reaction is preferably carried out in an organic solvent such as DMF, dimethyl sulphoxide, a lower alkanol, a chlorinated solvent or a lower ketone. Moderate temperatures, for example 10° to 200° C. are suitably employed. Conveniently the reaction is carried out at 50° to 70° C.

Compounds of formula (X), (XI) and (XIV) are known compounds or may be prepared from known compounds by known methods.

An alternative method for preparing compounds of formula (I) is by reacting a compound of formula (XV):

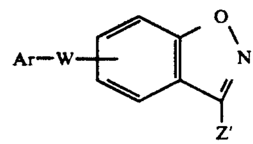

wherein Ar and W are as defined in relation to formula (I) and Z is a leaving group such as halogen with a compound of formula (XVI):

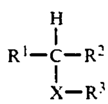

(XVI)

where X, $R^1$, $R^2$ and $R^3$ are as defined in relation to formula (I) in the presence of a base.

Suitable bases for use in the reaction include bases such as sodium hydride, alkali metal alkoxides and alkali metal bistrimethylsilyl amides.

The reaction is preferably carried out in an organic solvent such as dimethylformamide, dimethylsulphoxide, or tetrahydrofuran. Moderate temperatures, for example of from −78° C. to 100° C. are suitably employed Compounds of formula (XV) are novel and as such form a further aspect of the invention.

Compounds of formula (XV) are prepared from compounds of formula (XVII):

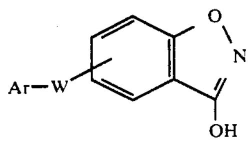

(XVII)

wherein Ar and W are as defined in relation to formula (I) by reaction with for example phosphorus tribromide, thionyl chloride, phosphorous oxychloride or phosphorous pentachloride at temperatures form 10° C. to 100° C.

Compounds of formula (XVI) and (XVII) are known compounds or can be prepared from known compounds by known methods.

If desired one or more of the following steps may be carried out:

i) when $R^3$ is alkoxycarbonyl hydrolysing to the corresponding acid.

ii) when $R^3$ is COOH esterifying or forming a salt, amide, sulphonamide, hydrazide or hydrazinium derivative.

iii) when $R^3$ is an alcohol, oxidation to the corresponding acid or aldehyde.

iv) when $R^3$ is alkoxycarbonyl, reduction to an alcohol.

v) when $R^3$ is an amide, dehydration to the corresponding nitrile.

vi) when $R^3$ is alkoxycarbonyl, n is 0 and $R^1$ or $R^2$ alkylation to the corresponding substituted ester.

vii) when $R^3$ is an amide, conversion to the corresponding thioamide.

The compounds of formula (I) are active as herbicides and therefore, in a further aspect the invention provides a process for severely damaging or killing unwanted plants which process comprises applying to the plants, or to the growth medium of the plants, an effective amount of a compound of formula (I) as hereinbefore defined.

The compounds of formula (I) are active against a broad range of weed species including monocotyledenous and dicotyledonous species. They may show some selectivity towards certain species; they may be used as selective herbicides in cotton, soya, maize, sugar beet and wheat crops.

The compounds of formula (I) may be applied directly to the plant (post-emergence application) or to the soil before the emergence of the plant (pre-emergence application). They are particularly useful when applied post-emergence.

The compounds of formula (I) may be used on their own to inhibit the growth of, severely damage, or kill plants but are preferably used in the form of a composition comprising a compound of the invention in admixture with a carrier comprising a solid or liquid diluent.

Therefore, in yet a further aspect, the invention provides plant growth inhibiting, plant damaging, or plant killing compositions comprising a compound of formula (I) as hereinbefore defined and an inert carrier or diluent.

Compositions containing compounds of formula (I) include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01% to 2% of active ingredient, while concentrated compositions may contain from 20% to 90% of active ingredient, although from 20% to 70% is usually preferred.

The solid compositions may be in the form of granules, or dusting powders wherein the active ingredient is mixed with a finely divided solid diluent, e.g. kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Surface-active agents may be of the cationic, anionic, or non-ionic type or mixtures thereof The cationic agents are, for example, quaternary ammonium compounds (e.g. cetyltrimethylammonium bromide). Suitable anionic agents are soaps; salts of aliphatic mono esters of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl and triisopropylnaphthalenesulphonic aid. Suitable non-ionic agents are the condensation products of ethylene oxide with fatty alcohols such as oleyl alcohol and cetyl alcohol, or with alkylphenols such as octyl- or nonyl-phenol (e.g. Agral 90) or octylcresol. Other non-ionic agents are the partial esters derived from long chain fatty acids and hexitol anhydrides, for example sorbitan monolaurate; the condensation products of the partial ester with ethylene oxide; and the lecithins; silicone surface active agents (water soluble surface active agents having a skeleton which comprises a siloxane chain e.g. Silwet L77). A suitable mixture in mineral oil is Atplus 411F.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene di-chloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. The concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the active ingredient(s). Dilute preparations ready for use may contain varying amounts of the active ingredients(s) depending upon the intended purpose; amounts of 0.01% to 10.0% and preferably 0.1% to 2%, by weight of active ingredient(s) are normally used.

A preferred form of concentrated composition comprises the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties to, and increase the viscosity of the concentrate. Examples of preferred suspending agents include hydrated colloidal mineral silicates, such as montmorillonite, beidellite, nontronite, hectorite, saponite, and suacorite. Bentonite is especially preferred. Other suspending agents include cellulose derivatives and polyvinyl alcohol.

The rate of application of the compounds of the invention of the will depend on a number of factors including, for example, the compound chosen for use, the identity of the plants whose growth is to be inhibited, the formulations selected for use and whether the compound is to be applied for foliage or root uptake. As a general guide, however, an application rate of from 0.001 to 20 kilograms per hectare is suitable while from 0.005 to 1 kilograms per hectare may be preferred.

The compositions of the invention may comprise, in addition to one or more compounds of the invention, one or more compounds not of the invention but which possess biological activity for example herbicides, fungicides, insecticides (optionally with an insecticide synergist) or a plant growth regulator. Accordingly in yet a still further embodiment the invention provides a herbicidal composition comprising a mixture of at least one herbicidal compound of formula (I) as hereinbefore defined with at least one other herbicide.

The other herbicide may be any herbicide not having the formula (I). It will generally be a herbicide having complementary action in the particular application. For Example herbicides, fungicides, insecticides (optionally with an insecticidal synergist) or a plant growth regulator.

Examples of useful complementary herbicides include

A. benzo-2,1,3-thiadiazin-4-one-2,2-dioxides such as bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, clopyralid, and their derivatives (e.g. salts, esters and amides);

C. 1,3 dimethylpyrazole derivatives such as pyrazoxyfen, pyrazolate and benzofenap;

D. Dinitrophenols and their derivatives (eg. acetates) such as dinoterb, dinoseb and its ester, dinoseb acetate;

E. dinitroaniline herbicides such as dinitramine, trifluralin, ethalfluralin, pendimethalin, oryzalin;

F. arylurea herbicides such as diuron, flumeturon, metoxuron, neburon, isoproturon, chlorotoluron, chloroxuron, linuron, monolinuron, chlorobromuron, daimuron, methabenzthiazuron;

G. phenylcarbamoyloxyphenylcarbamates such as phenmedipham and desmedipham;

H. 2-phenylpyridazin-3-ones such as chloridazon and norflurazon;

I. uracil herbicides such as lenacil, bromacil and terbacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vernolate, molinate, thiobencarb, butylate*, EPTC*, triallate, di-allate, esprocarb, tiocarbazil, pyridate, and dimepiperate;

*These compounds are preferably employed in combination with a safener such as dichlormid.

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, alachlor, propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, fluroglycofen or salts or ester thereof, nitrofen, bifenox, aciflurofen and salts and esters thereof, oxyfluorfen, fomesafen, chlornitrofen and chlomethoxyfen;

S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. cyclohexanedione herbicides such as alloxydim and salts thereof, sethoxydim, cycloxyidim, tralkoxydim, and clethodim;

U. sulfonyl urea herbicides such as chlorosulfuron, sulfometuron, metsulfuron and esters thereof; benzsulfuron and esters thereof such as DPX-M6313, chlorimuron and esters such as the ethyl ester thereof pirimisulfuron and esters such as the methyl ester thereof, 2-[3-(4-methoxy-6-methyl-1,3,5-triazin-zyl)-3-methylureidosulphonyl) benzoic acid esters such as the methyl ester thereof (DPX-LS300) and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylprop-ethyl, diflufenican;

X. amino acid herbicides such as glyphosate and glufosinate and their salts and esters, sulphosate and bialaphos;

Y. organoarsenical herbicides such as monosodium methanearsonate (MSMA);

Z. herbicidal amide derivative such as napropamide, propyzamide, carbetamide, tebutam, bromobutide, isoxaben, naproanilide and naptalam;

AA. miscellaneous herbicides including ethofumesate, cinmethylin, difenzoquat and salts thereof such as the methyl sulphate salt, clomazone, oxadiazon, bromofenoxim, barban, tridiphane, flurochloridone, quinchlorac, dithiopyr and mefanacet;

BB. Examples of useful contact herbicides include: bipyridylium herbicides such as those in which the active entity is paraquat and those in which the active entity is diquat.

The following Examples illustrate the invention:

EXAMPLE 1

This Example illustrates the preparation of compound in Table 1:

Step A

A suspension of 4,6-dihydroxycoumarin (0.5 g) in absolute ethanol (15 $cm^3$), containing hydroxylamine hydrochloride (0.58 g) and sodium metal (0.2 g), was heated at reflux for 9 hours. A grey precipitate formed during this period. After cooling to room temperature, the reaction mixture was concentrated under reduced pressure and the residue dissolved in aqueous sodium bicarbonate solution. The aqueous solution was extracted with diethyl ether. The ether extract was dried over anhydrous sodium sulphate, filtered and concentrated under reduced pressure to give a solid (0.09 g), 2,5-dihydroxyacetophenone oxime by NMR. The aqueous solution was acidified with concentrated hydrochloric acid and then extracted with diethyl ether. The ether extract was dried over anhydrous sodium sulphate, filtered and concentrated under reduced pressure to give a yellow-orange solid, 5-hydroxy-1,2-benzoxazol-3-ylacetic acid (0.29 g, 54%), m.p. 170° C. (decomposition).

$\delta_H$ ($CDCl_3$) 3.95(s)2H; 7.00(d)1H; 7.05(dd)1H; 7.50(d)1H; 9.60(broad s)1H; 12.80(broad s)1H.

Step B

Potassium carbonate (0.39 g) and 3-chloro-α,α,α,4,5-pentafluorotoluene (0.62 g) were added to a solution of 5-hydroxy-1,2-benzoxazol-3-ylacetic acid (0.5 g) in DMSO (20 $cm^3$). The reaction mixture was heated at reflux overnight, poured onto a mixture of ice and water, washed with diethyl ether, acidified and extracted with diethyl ether. The ether extract was dried with anhydrous sodium sulphate, filtered, and concentrated under reduced pressure to give a red solid (0.65 g). The solid was recrystallised from methylene chloride-hexane (50:50) to give the compound 1 (0.16 g, 17%), m.p. 127°-128° C.

EXAMPLE 2

This Example describes the preparation of compound 2 in Table I.

Step A 5-hydroxy-1,2-benzoxazol-3-yl acetic acid (0.5 g) produced as in step A of Example 1 was dissolved in methanol (30 $cm^3$) containing concentrated sulphuric acid (2 $cm^3$). The reaction mixture was heated at reflux for 5½ hours, allowed to stand at room temperature overnight, heated at reflux for 6¼ hours, allowed to stand at room temperature, heated at reflux for 7 ¾ hours and finally allowed to stand at room temperature overnight. The solution was poured into ice/water and extracted with diethyl ether. The ether extract was dried over anhydrous sodium sulphate, filtered and concentrated under reduced pressure. The residue (0.46 g) was further purified by preparative thin layer chromatography (silica/chloroform-acetone, 9:1) to give methyl 5-hydroxy-1,3-benzisoxazol-3-yl acetate a white solid (0.3 g,56%).

δH ($CDCl_3$): 3.6(s)3H; 4.1(s)2H; 6.95(d)1H; 7.05(dd)1H; 7.5(d)1H; 9.6(s)1H.

Step B

A sample of the methyl acetate, prepared as in step A (5.47 g) was dissolved in DMSO (50 $cm^3$). Potassium carbonate (7.29 g) and 6-chloro-α,α,α,4,5-pentafluorotoluene (7.04 g) were added to the solution.

The reaction mixture was heated at 100° C. for 1¼ hours, allowed to cool and then poured into water. The aqueous mixture was extracted with diethyl ether. The ether extract was dried over anhydrous sodium sulphate, filtered and concentrated at reduced pressure to give the crude product, an orange-black oil (11.48 g). The crude product was further purified by column chromatography (silica/hexane-diethylether, 7:3) to give compound 2 as a viscous orange oil (6.55 g, 62%).

EXAMPLE 3

This Example describes the preparation of compound 1 in Table I.

Compound 2 as produced in Example 2, (0.7 g) was dissolved in THF (15 $cm^3$). Water (5 $cm^3$) and potassium hydroxide (0.1 g) were added. The reaction mixture was then heated at reflux for 6 hours and allowed to stand at room temperature overnight. The solution was poured into water and extracted with diethyl ether. The ether extract was washed with brine, dried over anhydrous sodium sulphate, filtered and concentrated under reduce pressure to give an orange solid (0.22 g) which was starting material by n.m.r. The aqueous solution was acidified with concentrated hydrochloric acid and extracted with diethyl ether. The ether extract was washed with brine, dried over anhydrous sodium sulphate, filtered and concentrated under reduced pressure to give compound 1 as a white solid (0.49 g, 73%).

EXAMPLE 4

This Example illustrates the preparation of compound 3 of Table I.

Compound 2 as produced in Example 2, (0.5 g) was dissolved in tetrahydrofuran (10 $cm^3$) and the solution cooled to −15° C. with stirring. A 1.OM solution of lithium bis(trimethylsilyl)amide in toluene (1.42 $cm^3$) was added dropwise and the solution stirred for a further 1 hour. (During this period the reaction mixture cooled to −25° C.) Methyl iodide (0.5 $cm^3$) was added and the reaction mixture was allowed to warm to room temperature overnight. The reaction mixture was poured into water and the aqueous solution was extracted with diethyl ether. The ether extract was washed with brine, dried over anhydrous sodium sulphate, filtered and concentrated at reduced pressure. The residue (0.3 g) was purified by preparative thin layer chromotography (silica/hexane-diethylether, 7:3) to give compound 3, a yellow solid (0.08 g, 14%).

EXAMPLE 5

This Example describes the preparation of compound 4 in Table I.

Bromine (0.14 g) in a small volume of methylene chloride was added to a solution of compound 2 produced as described in Example 2, (0.4 g) in a mixture of methylene chloride (10 $cm^3$) and acetic acid (10 $cm^3$). The mixture was then heated at reflux for 1 ¾ hours. After cooling to room temperature, the mixture was poured into water and extracted with diethyl ether. The ether extract was washed with aqueous sodium bicarbonate solution, dried over anhydrous sodium sulphate, filtered and concentrated under reduced pressure. The residue (0.44 g) was purified by preparative thin layer chromatography (silica/hexanediethyl ether, 70:10) to give compound 4, as a white solid (0.2 g,42%).

EXAMPLE 6

This Example describes the preparation of compound 5 in Table I.

A solution of the compound 2, produced as described in Example 2 (0.5 g) in dry THF (10 $cm^3$) was cooled to −15° C. A 0.5M solution of potassium bis(trimethylsilyl)amide in toluene (2.72 $cm^3$) was added and the mixture stirred at −15° C. for 1½ hours. During this time the solution went orange in colour. Methyl iodide (0.1 g) in dry tetrahydrofuran (3.5 $cm^3$) was added dropwise to the stirred solution. When the addition was complete, the solution was allowed to warm to room temperature, poured into water and extracted with diethyl ether. The ether solution was washed with brine, dried over anhydrous sodium sulphate, filtered and concentrated under reduced pressure to give an oil (0.5 g). The oil was purified by preparative thin layer chromatography (silica/hexane-diethyl ether, 7:3) to give compound 5 (0.33 g, 64%), as a yellow oil.

Compounds 6 and 90 were prepared in an analagous manner using appropriate reactants.

EXAMPLE 7

This Example illustrates the preparation of compound 7 in Table I.

Concentrated sulphuric acid (2 $cm^3$) was added to a solution of compound 2 produced as in Example 2 (0.52 g) in ethanol (30 $cm^3$). The solution was heated at reflux for 2 hours, allowed to cool to room temperature and poured into water. The aqueous mixture was extracted with diethyl ether. The ether extract was washed with aqueous sodium bicarbonate solution, dried over anhydrous sodium sulphate, filtered and concentrated under reduced pressure. The residue (0.49 g) was purified by preparative thin layer chromatography (silica/hexane-diethyl ether, 3) to give compound 7 (0.41 g,76%), as a pale yellow solid, m.p. 59°-60° C.

Compounds 10, 11 and 95 were produced in an analagous manner using appropriate reactants.

EXAMPLE 8

This Example illustrates the preparation of compound in Table I.

A 0.5 M solution of potassium bis(trimethylsilyl)amide in toluene (2.8 $cm^3$) was added to a cooled solution of compound 7 produced as in Example 7 (0.53 g) in dry THF (10 $cm^3$) at −15° C. The solution turned orange and was stirred at −15° C. for 1½ hours. After a solution of methyl iodide (0.16 g) in dry THF (3.5 $cm^3$) had been added, the reaction mixture was allowed to warm to room temperature over night and poured into water. The aqueous mixture was extracted with diethyl ether. The ether extract was washed with brine, dried over anhydrous sodium sulphate, filtered and concentrated under reduced pressure. The residue (0.57 g) was further purified by preparative thin layer chromatography (silica/hexane-diethyl ether, 7:3) to give the compound 8 (0.36 g, 66%) as a pale yellow oil.

Compounds 9, 15 and 16 were produced in an analagous manner using appropriate reactants.

EXAMPLE 9

This example illustrates the preparation of compound 12 in Table I.

A catalytic quantity of dimethylaminopyridine and dicyclohexylcarbodiimide (0.26 g) were added to a solution of compound 1 (prepared as in Example 1) (0.45 g) in dry dichloromethane (10 $cm^3$) which was cooled with an ice bath. Propargyl alcohol (0.07 g) was added, the ice bath removed and the reaction mixture stirred and allowed to warm to room temperature. After 3 hours, a precipitate was removed by filtration through hiflow and washed with dichloromethane. The washings and filtrate were combined and concentrated under reduced pressure. The residue (0.60 g) was purified by preparative thin layer chromatography (silica/-hexane-diethylether, 7:3) to give compound 12 (0.22 g, 44%) as a very pale yellow solid, m.p. 66°-67° C.

EXAMPLE 10

This Example illustrates the preparation of compound 3 in Table I.

Compound 1 prepared as in Example 1 (0.89 g), a catalytic quantity of DMAP and n-butanol (0.19 g) were dissolved in dry dichloromethane (7 $cm^3$) and the solution cooled with an ice/salt bath. DCC (0.5 g) was added and the ice bath removed. The reaction mixture was stirred and allowed to warm to room temperature. After 3 hours, a precepitate was removed by filtration through hiflow and washed with dichloromethane. The washings and filtrate were combined and concentrated under reduced pressure. The material obtained (1.06 g) was purified by preparative thin layer chromatography (silica/hexane-diethyl ether, 7:3) to give compound 13 (0.71 g, 70%) as an almost white solid, m.p. 50°-51° C.

Compounds 17, 18, 40, 41, 92 and 98 were produced in an analogous manner using appropriate reagents and starting materials.

EXAMPLE 11

This example illustrates the preparation of compound 14 in Table I.

Compound 5 in Table I prepared as in Example 6 (1.35 g) was dissolved in THF (7 $cm^3$). Water (5 $cm^3$) and potassium hydroxide (0.2 g) were added. The mixture was heated at reflux for 3½ hours. After cooling, the mixture was poured onto ice. The aqueous solution was washed with diethyl ether, acidified with concentrated HCl and extracted with diethyl ether. The ether extract was washed with brine, dried over anhydrous sodium sulphate, filtered and concentrated under reduced pressure to give compound 14 as a white solid (1.07 g,83%), m.p. 133°-135° C.

EXAMPLE 12

This example illustrates the preparation of compound 19 in Table I.

Sodium hydride as a 60% suspension in oil (0.23 g) and ∝,∝,∝3,4,5-hexafluorotoluene were added to a solution of methyl 5-hydroxy-1,2-benzoxazol-3-ylacetate (1.06 g), produced as in step A of Example 2, in DMF (10 $cm^3$). The mixture was stirred at room temperature for 23 hours and then poured into water. The aqueous solution was extracted with diethyl ether. The ether extract was washed with brine, dried over anhydrous sodium sulphate, filtered and the filtrate concentrated under reduced pressure. The material obtained (0.9 g) was purified by preparative thin layer chromatography (silica/hexane-ether, 7:3) to give compound 19 as a pale yellow oil (0.36 g, 18%) consisting of a mixture of compound 19 (84%) an isomer (10%) and compound 2 (6%). (Compound 2 arose from 6-chloro-∝,∝,∝,4,5-pentafluorotoluene present as an impurity in the hexafluorotoluene.) The compounds of the mixture were inseparable by either tlc or glc and were quantified by $^{19}F$ NMR.

EXAMPLE 13

This example illustrates the preparation of compound 20 in Table I.

Compound 19 (3.41 g), prepared as described in Example 12, was dissolved in THG (10 $cm^3$). Water (5 $cm^3$) and potassium hydroxide (0.54 g) were added. The reaction mixture was heated at reflux for 3½ hours. After cooling, the mixture was poured into water and washed with diethyl ether, acidified with concentrated HCl, and extracted with diethyl ether. The ether extract was washed with brine, dried over sodium sulphate, filtered, and concentrated under reduced pressure, to give compound 20 as a white solid, m.p. 120°-121° C, as the major component (84%) of a mixture (2.9 g,88%), with a regioisomer of compound 20 (12%) and compound 1 (4%), a white solid, m.p. 120°-121° C.

The components of the mixture were quantified by $^{19}F$ NMR.

EXAMPLE 14

This example describes the preparation of compound 21 in Table I.

Compound 20 (0.52 g), prepared as described in Example 13, a catalytic quantity of DMAP and ethanol (0.07 g) were dissolved in dry dichloromethane and the solution cooled with an ice/salt bath. DCC (0.33 g) was added, the ice bath removed and the mixture allowed to warm. After stirring for 2½ hours at room temperature, the mixture was filtered through hiflow and the residue washed with dichloromethane. The washings and filtrate were combined and concentrated under reduced pressure. The material obtained (0.62 g) was purified by preparative thin layer chromatography (silica/hexane-diethylether, 7:3) to give compound 21 as the major component (85%) of a mixture (0.44 g,79%), a pale yellow oil. The mixture consisted of compound 21 (85%), a regioisomer of compound 21 (2%) and compound 7 in Table I (3%). The components of the mixture were identified and quantified by $^{19}F$ NMR.

Compounds 22, 23, 24 and 25 were produced as similar mixtures in an analogous manner using appropriate reagents and starting materials.

EXAMPLE 15

This Example describes the preparation of compound 26 in Table I.

A 0.5 M solution of potassium bis(trimethylsilyl)amide in toluene (28 $cm^3$) was added to a solution of compound 19 produced as in Example 12 (4.87 g) in dry THF (7 $cm^3$) cooled with a dry ice/ethanediol bath. The mixture was cooled and stirred for 2½ hours. Methyl iodide (4.36 $cm^3$ of a methyl iodide (10 $cm^3$) in THF (40 $cm^3$) solution) was added and the reaction mixture allowed to warm to room temperature overnight. The reaction mixture was poured into water and extracted with brine, dried over anhydrous sodium sulphate, filtered and concentrated under reduced pressure. The material obtained (6.28 g) was purified by column chromatography (silica 4×35 cm/hexane-diethyl ether, 7:3) to give compound 26 as the major component of a mixture which was a pale yellow oil (3.49 g, 67%). The mixture consisted of compound 26 (79%), a regioisomer of compound 26 (18%) and compound 8 (3%) by $^{19}F$ NMR.

EXAMPLE 16

This example describes the preparation of compound 27 in Table I.

Compound 26 (2.93 g), prepared as described in Example 15, was dissolved in THF (10 $cm^3$). Water (5 $cm^3$) and potassium hydroxide (0.45 g) were added and the mixture was heated at reflux for 23 hours. After cooling, the reaction mixture was poured into water. The aqueous solution was washed with diethyl ether, acidified with concentrated HCl, and extracted with diethyl ether. The ether extract was washed with brine, dried over anhydrous sodium sulphate, filtered and concentrated under reduced pressure to give compound 27 as a component of mixture which was a white solid (2.22 g, 78%), m.p. 105°-106° C. The mixture consisted of compound 27 (82%), a regioisomer of compound 27 (15%) and compound 14 (3%) by $^{19}F$ NMR.

EXAMPLE 17

This Example describes the preparation of compound 28 in Table I.

Compound 27 (0.45 g), prepared as described in Example 16, ethanol (0.06 g) and a catalytic quantity of DMAP were dissolved in dry dichloromethane (10 $cm^3$) and the solution cooled with an ice/salt bath. DCC (0.26 g) was added and the ice bath removed. The reaction mixture was allowed to warm and stirred at room temperature 1.75 hours. A precipitate was removed by filtration through hiflow and washed with dichloromethane. The filtrate and washings were combined and concentrated under reduced pressure to give an oil. The oil was purified by preparative thin layer chromatography (silica/hexane-diethylether, 8:2) to give compound 28 as the major component of a mixture which was a pale yellow oil (0.31 g, 64%). The mixture consisted of compound 28 (82%), a regioisomer of compound 28 (15%) and compound 8 (3%) by $^{19}F$ NMR.

Compounds 29, 30, 31 and 32 in Table I were produced as components of similar mixtures in an analogous manner using appropriate reagents and starting materials.

EXAMPLE 18

This Example describes the preparation of compound 33 in Table I.

2-Fluoro-5-trifluoromethylbenzonitrile (3.21 g) and potassium carbonate (3.86 g) were added to a solution of methyl 5-hydroxy-1,2-benzoxazol-3-ylacetate (3 g), produced as describe in step A of Example 2, in dry DMSO (15 $cm^3$). The reaction mixture was heated at 100° C. for 3½ hours. After cooling, the mixture was poured into water and extracted with diethyl ether. The ether extract was washed with brine, dried over anhydrous sodium sulphate, filtered and concentrated under reduced pressure. The material obtained (4.73 g) was purified by column chromatography (silica 3×30 cm/hexane-diethyl ether, 1:1) to give compound 33 (2.61 g, 50%) as a orange/yellow solid, 127°-129° C.

Compounds 42, 54, 60, 71 and 77 were produced in an analogous manner using appropriate reagents and starting materials.

EXAMPLE 19

This example describes the preparation of compounds 34 and 35 in Table I.

A 0.5 M solution of potassium bis(trimethylsilyl)amide in toluene (7.8 $cm^3$) was added to solution of compound 33, produced as described in Example 18, (1.35 g) in dry THF (5 $cm^3$) cooled with a dry ice/ethanediol bath. After stirring and cooling for 1 hour, methyl iodide (0.55 g in 4 $cm^3$ THF) was added and the reaction mixture allowed to warm to room temperature overnight. The mixture was poured into water and extracted with diethyl ether. The ether extract was washed with brine, dried over anhydrous sodium sulphate, filtered and concentrated under reduced pressure to give a semi-solid residue. The residue (0.65 g) was purified by preparative thin layer chromatograph (silica/hexane-diethyl ether, 1:1) to give two compounds.

The faster eluting material was compound 35 (0.21 g, 8%), a solid, m.p. 121°-124° C.

Compound 45 was prepared in an analogous manner using appropriate reagents.

The slower eluting material was compound 34 (0.71 g, 51%) a soft solid.

Compound 44, 56, 62, 78 were prepared in an analogous manner using appropriate reagents and starting materials.

EXAMPLE 20

This Example describes the preparation of compound 36 in Table I.

Water (5 $cm^3$) and potassium hydroxide (0.16 g) were added to a solution of compound 33 (1.0 g), produced as described in Example 18, in THF (10 $cm^3$). The reaction mixture was heated at reflux at for 4 ½ hours, then left at room temperature over the weekend. The mixture was poured into water, washed with diethyl ether, acidified with concentrated HCl and extracted with diethyl ether. The ether extract was washed with brine, dried over anhydrous sodium sulphate, filtered and concentrated under reduced pressure to give compound 36 (0.79 g, 81%) as a pale yellow solid, m.p. 67°-70° C.

Compounds 38, 43, 47, 55, 58 and 61 were produced in an analogous manner using appropriate reagents and starting materials.

EXAMPLE 21

This Example described the preparation of compound 37 in Table I.

Compound 36 (0.58 g), prepared as described in Example 20, ethanol (0.08 g) and a catalytic quantity of DMAP were dissolved in dry dichloromethane (5 $cm^3$) and the solution cooled with a salt/ice bath. DCC (0.36 g) was added and the salt/ice bath removed. After stirring at room temperature overnight, the mixture was filtered through hiflow and the residues washed with dichloromethane. The washings and filtrate were combined and concentrated under reduced pressure. The material obtained (0.64 g) was purified by preparative thin layer chromatography (silica/hexane-diethyl ether, 1:1) to give compound 37 (0.35 g, 56%) as an off white solid, m.p. 91°-92° C.

Compounds 39, 46, 57 and 59 were produced in an analogous manner using appropriate reagents and starting materials.

EXAMPLE 22

The Example describes the preparation of compound 48 in Table I.

A mixture of chloropentafluorobenzene (3 g), potassium carbonate (3.86 g) and methyl 5-hydroxy-1,2-benzoxazol-3-ylacetate (3 g), prepared as described in step A of Example 2, in dry DMSO (15 $cm^3$) was heated at 100° C. for 3 hours. After cooling, the mixture was poured into water and extracted with diethyl ether. The ether extract was washed with brine, dried over anhydrous sodium sulphate, filtered and concentrated under reduced pressure. The material obtained (5:43 g) was purified by column chromatography (silica 3×30 cm/hexane-diethyl ether, 7:3) to give compound 48 as the major component of a mixture, a pale yellow solid (3.53 g, 65%), m.p. 72°-74° C. The mixture consisted of compound 48 (77%) and 2 isomers by $^{19}F$ NMR.

EXAMPLE 23

This Example describe the preparation of compound 49 in Table I.

A 0.5 M solution of potassium bis(trimethylsilyl)amide in touluene (9.7 $cm^3$) was added to a solution of compound 48 (1.72 g), prepared as described in Example 22, in dry THF (10 $cm^3$) cooled by a dry ice/ethanediol bath. After cooling and stirring for 1.75 hours, methyl iodide (0.69 g in 3.78 $cm^3$ dry THF) was added, and the reaction mixture then allowed to warm to room temperature overnight. The mixture was poured into water and extracted with diethyl ether. The ether extract was washed with brine, dried over anhydrous sodium sulphate, filtered, and concentrated under reduced pressure. The concentrate (1.94 g) was purified by preparative thin layer chromatography (silica/hexane-diethylether, 7:3) to give compound 49 as a component of mixture, a pale yellow oil (0.98 g, 55%), containing compound 49 (81%) and two other isomers of compound 49 (15% and 4%) by $^{19}F$ NMR.

EXAMPLE 24

This Example described the preparation of compound 50 in Table I.

Water (5 $cm^3$) and potassium hydroxide (0.24 g) were added to a solution of compound 48 (1.51 g), prepared as described in Example 22, in THF (10 $cm^3$) and the mixture was heated at reflux for 0.75 hour. After cooling, the mixture was washed with diethyl ether, acidified with concentrated HCl and extracted with diethyl ether. The ether extract was washed with brine, dried over anhydrous sodium sulphate, filtered and concentrated under reduced pressure to give compound 50 as the major component (75% by $^{19}F$ NMR) of a mixture of isomers, a green solid (1.56 g, 100%) m.p. 138°-140° C.

Compound 52 was prepared in an analogous manner using appropriate reagents and starting material.

EXAMPLE 25

This Example describes the preparation of compound 51 in Table I.

Compound 50 (0.4 g), prepared as described in Example 24, ethanol (0.05 g) and a catalytic quantity of DMAP were dissolved in dry dichloromethane (10 $cm^3$) and the solution cooled with an ice/salt bath. DCC (0.24 g) was added and the ice/salt bath removed. After stirring at room temperature overnight, the mixture was filtered through hiflow and the residues washed with dichloromethane. The combined washings and filtrate were concentrated under reduced pressure. The material obtained was purified by preparative thin layer chromatography (silica/hexane-diethyl ether, 7:3) to give compound 51 as the major component (79% by $^{19}F$ NMR) of a mixture of isomers, a white solid (0.26 g, 60%), m.p. 52°-53° C.

Compound 53 was prepared in an analogous manner from appropriate reagents and starting material.

EXAMPLE 26

This Example describes the preparation of compound 63 in Table I.

Compound 1 (0.3 g), prepared as described in Example 3, methylamine hydrochloride (0.08 g), a catalytic quantity of DMAP, and triethylamine (0.12 g) were dissolved in dry dichloromethane and the solution cooled with an ice/salt bath. DCC (0.17 g) was added and the ice/salt bath removed. After stirring at room temperature overnight, the reaction mixture was filtered through hiflow and the residues washed with dichloromethane. The washings and filtrate were combined and concentrated under reduced pressure. The material obtained (0.51 g) was purified by preparative thin layer chromatography (silica/diethylether) to give compound 63 (0.12 g, 39%) as a white solid, m.p. 194°-195° C.

Compound 64 and 66 were prepared in an analogous procedure using appropriate reagents and starting materials.

EXAMPLE 27

This Example describes the preparation of compound 65 in Table I.

Step A

Potassium hydroxide (4 pellets) was added to a solution of compound 5 (0.55 g), prepared as described in Example 6, in methanol (15 $cm^3$) and the mixture heated at reflux for 1 hour. After cooling the mixture was poured into water, washed with diethyl ether, acidified with concentrated HCl and extracted with diethyl ether. The ether extract was washed with brine, dried over anhydrous sodium sulphate, filtered and concentrated under reduced pressure. The white solid (0.40 g) was used in step B without further purification.

Step B

The solid (0.38 g) from step A was dissolved in methanol (25ml). After the addition of concentrated sulphuric acid (2 $cm^3$) the mixture was heated at reflux for 6 hours. After cooling, the mixture was poured into water and extracted with diethyl ether. The ether extract was washed with brine, dried over anhydrous sodium sulphate, filtered and concentrated under reduced pressure. The material obtained (0.28 g) was purified by preparative thin layer chromatography (silica/hexane-diethylether, 7:3) to give compound 65 (0.07 g, 17%) a white solid, m.p. 85°-86° C.

EXAMPLE 28

This Example describes the preparation of compound 67 in Table I.

Step A

The acid (0.31 g), compound 14 prepared as described in Example 11, was suspended in thionyl chloride (5 $cm^3$). The suspension was heated with hot air to form a solution, which was allowed to stand at room temperature for 1 hour. The thionyl chloride was removed under reduced pressure at 45° C. for 30 minutes to give a yellow oil, a crude acid chloride.

Step B

The oil from step A was dissolved in dry dichloromethane (10 $cm^3$) and the solution cooled with an ice/salt bath. Excess dimethylamine was added by pipette, the ice bath removed and the reaction mixture allowed to warm to room temperature. After stirring at room temperature for 1½ hours, the reaction mixture was poured into water and extracted with dichloromethane. The dichloromethane extract was washed with dilute hydrochloric acid, aqueous sodium bicarbonate and brine, dried over anhydrous sodium sulphate, filtered and concentrated under reduced pressure. The material obtained (0.3 g) was purified by preparative thin layer chromatography (silica/ether) to give compound 67 (0.15 g, 45%) as initially a colourless oil, which slowly solidified to a soft solid on standing.

EXAMPLE 29

This Example describes the preparation of compound 68.

Compound 2 (0.3 g) prepared as described in Example 2, was dissolved in methanol (5 $cm^3$). Aqueous ammonium hydroxide solution (approximately 2 $cm^3$) was added and a precipitate formed. The mixture was stirred at room temperature for 1½ hours. After the further addition of ammonium hydroxide solution (approximately 4 $cm^3$) sufficient methanol was added to dissolve the precipitate and the reaction mixture was heated at reflux for 3 ¼ hours. The mixture was allowed to stand at room temperature overnight, poured into water and extracted with diethyl ether. The ether extract was washed with dilute hydrochloric acid and brine, dried over anhydrous sodium sulphate, filtered and concentrated under reduced pressure. The acid washings were made basic and extracted with diethyl ether. The second diethyl ether extract was washed with brine, dried over anhydrous sodium sulphate, filtered and concentrated under reduced pressure. The material from the two ether extractions (0.17 g and 0.04 g respectively) were combined and purified by preparative thin layer chromatography (silica/ether with a few drops of acetic acid) to give a compound 68 (0.08 g, 28%) as a white solid, m.p. 181°-182° C.

EXAMPLE 30

This Example describes the preparation of compound 69 in Table 1.

Crude acid chloride, prepared from compound 14 (0.3 g) prepared as described in step A of Example 28, was dissolved in dry dichloromethane (10 $cm^3$) and the solution cooled with an ice/salt bath. 1,1-Dimethylhydrazine (0.05 g) and triethylamine (0.08 g) were added, the ice bath removed and the reaction mixture. After stirring for 1 hour at room temperature. After stirring for 1 hour at room temperature, the mixture was diluted with dichloromethane to approximately 100 $cm^3$ and the resulting solution washed with water, aqueous sodium bicarbonate and brine, dried over sodium sulphate, filtered and concentrated under reduced pressure. The material obtained (0.33 g) was purified by preparative thin layer chromatography (silica/diethyl ether) to give compound 69 as a component of a mixture (0.12 g). Further purification by preparative thin layer chromatography (silica/diethyl ether acidified with acetic acid) gave compound 69 (0.10 g, 30%) as a white solid, m.p. 172°-173° C.

Compound 70 was prepared in an analogous manner from compound 1 using appropriate reagents and starting material.

EXAMPLE 31

This Example describes the preparation of compound 72 in Table I.

1,2,3-Trichloro-5-trifluoromethylbenzene (3.29 g) and potassium carbonate (3.3 g) were added to a solution of methyl 5-hydroxy-1,2-benzoxazol-3-ylacetate (2.5 g), prepared as described in step A of Example 2, in dry DMSO (15 $cm^3$). The reaction mixture was heated at 100° C. for 3.75 hours. After cooling, the mixture was poured into water and extracted with diethyl ether. The ether extract was washed with brine, dried over anhydrous sodium sulphate, filtered and concentrated under reduced pressure. The material obtained (3.78 g) was purified by preparative thin layer chromatography to give compound 72 as the major component (92%) of a mixture of isomers (1.43 g, 28%) a white solid, m.p. 99°-100° C.

EXAMPLE 32

This Example describes the preparation of compound 73 in Table I.

Water (5 $cm^3$) and potassium hydroxide (0.07 g) were added to a solution of compound 72 (0.5 g), prepared as described in Example 31, in THF (10 $cm^3$). The reaction mixture was heated at reflux for 2 hours. After cooling, the mixture was poured into water, washed with diethyl ether, acidified with concentrated HCl, and extracted with diethyl ether. The ether extract was washed with brine, dried over anhydrous sodium sulphate, filtered and concentrated under reduced pressure to give compound 73 (0.27 g, 56%) as a white solid, m.p. 175°-176° C.

Compound 75 was prepared in an analogous manner using appropriate reagents and starting material.

EXAMPLE 33

This Example describes the preparation of compound 74 in Table I.

A 0.5M solution of potassium bis(trimethylsilyl)amide in toluene (3.58 $cm^3$) was added to a solution of compound 72, (0.68 g), prepared as described in Example 31, in dry THF (10 $cm^3$) cooled with a dry ice/ethanediol bath. After stirring and cooling for 1 hour, a solution of methyl iodide (0.25 g) in dry THF (2.74 $cm^3$) was added and the reaction mixture allowed to warm to room temperature over 7 hours. The mixture was poured into water and extracted with diethyl ether. The ether extract was poured into water, washed with brine, dried over anhydrous sodium sulphate, filtered and concentrated under reduced pressure. The material obtained (0.78 g) was purified by preparative thin layer chromatography to give compound 74 as the major component (92%) of a mixture of isomers (0.45 g, 64%), a white solid m.p. 67°-68° C.

EXAMPLE 34

This Example describes the preparation of compound 76 in Table I.

Compound 2 (0.29 g) prepared as in Example 2 was dissolved in acetic acid (5.7 $cm^3$) containing chlorine (0.06 g). The reaction mixture was stirred at room temperature overnight. Analysis by tlc indicated that unreacted compound 2 remained. The mixture was heated at reflux for 1 hour, then more chlorine (0.04 g) in acetic acid (3 $cm^3$) was added and the mixture was heated at reflux for a further 1.75 hour. A further addition of chlorine (0.02 g) in acetic acid (2 $cm^3$) was made and the mixture heated at reflux for an additional 1½ hours. After cooling to room temperature, the mixture was diluted with dichloromethane, washed with water, aqueous sodium bicarbonate and brine, dried over anhydrous sodium sulphate, filtered and concentrated under reduced pressure. The material obtained (0.28 g) was purified by preparative thin layer chromatography (silica/hexane-diethyl ether, 7:3, double elution) to give compound 76 (0.16 g, 51%) as a colourless oil.

EXAMPLE 35

This Example describes the preparation of compound 79 in Table I.

Compound 2 (0.4 g) as prepared in Example 2, was dissolved in a solution of bromine (0.27 g) in acetic acid (5 $cm^3$). The reaction mixture was heated at reflux for 5.75 hours. After cooling, the mixture was poured into water and extracted with dichloromethane. The extract was washed with aqueous sodium bicarbonate and brine, dried over anhydrous sodium sulphate, filtered and concentrated under reduced pressure. The material obtained (0.42 g) was purified by preparative thin layer chromatography (silica/hexane-diethyl ether, 9:1) to give compound 79 as the major component (83%) of a mixture with compound 4 (17%).

EXAMPLE 36

This Example describes the preparation of compound 80 in Table I.

Step A

Compound 2 (0.5g), prepared as described in Example 2, and potassium hydroxide (0.38 g) were dissolved in methanol (15 $cm^3$) and the solution was heated at reflux for 3.75 hours. After cooling, the solution was poured into water, washed with diethylether, acidified with concentrated HCl and extracted with diethyl ether. The ether extract was washed with brine, dried over anhydrous sodium sulphate, filtered, and concentrated under reduced pressure to give a white solid (0.45 g).

Step B

The white solid (0.45 g), prepared as described in step A, was dissolved in methanol (10 $cm^3$) and concentrated sulphuric acid (1 $cm^3$) was added. The solution was heated at reflux for 4 hours. After cooling, the solution was poured into water and extracted with diethyl ether. The ether extract was washed with aqueous sodium bicarbonate and brine, dried over anhydrous sodium sulphate, filtered and concentrated under reduced pressure. The material obtained (0.58 g) was purified by preparative thin layer chromatography (silica/hexane-diethyl ether, 7:3) to give compound 80 (0.19 g, 37%) as a white solid of m.p. 128°-130° C.

EXAMPLE 37

This Example describes the preparation of Compound No. 81 in Table I.

Compound No. 70, prepared as described in Example 30 (0.29 g) was dissolved in methanol (15 $cm^3$) and methyl iodide (1 $cm^3$) was added. The reaction flask was covered with tin foil and left at room temperature for 3 days, after which the reaction mixture was concentrated under reduced pressure to give a yellow oil. Trituration with diethyl ether, produced a semi-solid which was washed with ether three times, dissolved in chloroform and re-precipitated with ether. The residue was dried under reduced pressure, to give compound No. 81 (0.2 g, 67%) as a yellow solid m.pt 87°-90° C.

EXAMPLE 38

This Example describes the preparation of Compound No. 82 in Table I.

Compound No. 68 (0.23 g) prepared as described in Example 29, and triethylamine (0.13 g) were dissolved in dry dichloromethane (15 $cm^3$) and the solution cooled using an ice/salt bath. Trichloroacetyl chloride (0.12 g) was added dropwise and the ice bath removed. After stirring at room temperature for 1½ hours, the mixture was concentrated under reduced pressure. The residue was dissolved in diethyl ether, washed with water and then with brine, dried over anhydrous sodium sulphate, filtered and concentrated under reduced pressure. The material obtained (0.20 g) was purified by preparative thin layer chromatography (silica/hexane-diethylether, 7:3) to give compound No. 82 (0.08 g,37%) as a white solid, m.p 90°-92° C.

Compound No. 87 was prepared in an analagous procedure from Compound No. 86 using appropriate reagents and starting materials.

EXAMPLE 39

This Example describes the preparation of Compound No. 83 in Table I.

Lithium alumuniumhydride (0.12 g) was suspended in dry diethyl ether (15 mls) under a nitrogen atmosphere and cooled using an ice bath. A solution of Compound No. 2 (0.6 g) prepared as described in Example 2, in dry diethyl ether (5ml) was added slowly. The ice bath was removed and the solution allowed to warm to room temperature overnight.

A mixture of water (5 $cm^3$) and dioxane (5 $cm^3$) were added to the suspension causing effervescence. The mixture was further diluted with diethyl ether, washed with water, brine, dried over anhydrous sodium sulphate, filtered and concentrated under reduced pressure.

The material obtained (0.52 g) was purified by preparative thin layer chromatography (silica/hexanediethylether, 1:1) to give compound No. 83 (0.15 g 27%) as a white solid, m.p 87°-89° C.

EXAMPLE 40

This Example describes the preparation of Compound No. 84 in Table I.

Step A

Compound No. 1 (0.3 g), prepared as described in Example 3, was dissolved in thionyl chloride (10 $cm^3$) by gentle heating with hot air. The solution was allowed to stand at room temperature for ¾ hour and then concentrated under reduced pressure for 30 minutes to give a gum, the crude acid chloride.

Step B

The gum from Example 40 Step A, was dissolved in dry dichloromethane (10 $cm^3$) and the solution cooled with an ice bath. Benzyl alcohol (0.09 g) followed by triethylamine (0.08 g) were added giving white fumes, the ice bath was removed and the mixture allowed to warm to room temperature overnight.

The reaction mixture was diluted with dichloromethane, washed with water, dilute hydrochloric acid, aqueous sodium bicarbonate, and brine, dried over anhydrous sodium sulphate, filtered and concentrated under reduced pressure. The material obtained (0.33 g) was purified by preparative thin layer chromatography (silica/hexane-diethylether, 9:1) to give Compound No. 84 (0.19 g 54%) as a white solid m.p 82°-83° C.

Compound No. 85 was prepared in an analogous manner from Compound No. 1 using appropriate reactants.

EXAMPLE 41

25 This Example describes the preparation of Compound No. 86 in Table I.

Compound No. 5 (0.41 g), prepared as described in Example 6, was dissolved in methanol (20 $cm^3$). Aqueous ammonium hydroxide (approximately 4 $cm^3$) was added until a white precipitate just began to form. The mixture was stirred at room temperature for 2 days during which time white solid precipitated out of solution. Water was added to the mixture, the white solid was filtered off and dried by vacuum dessicator, to give Compound No. 86 (0.22 g 56%) as a white solid m.p 163°-164° C.

EXAMPLE 42

This Example describes the preparation of Compound No. 88 in Table I.

Crude acid chloride, prepared as described in Step A of Example 40 from Compound No. 1 (0.3 g) which was produced as in Example 3, was dissolved in dry dichloromethane (10 $cm^3$) and the solution cooled using an ice bath.

2-methoxyethylamine (0.06 g) and triethylamine (0.09 g) were added, the ice bath removed and the reaction mixture allowed to warm to room temperature. After leaving for 2 days at room temperature, the mixture was diluted with dichloromethane, washed with water, brine, dried over anhydrous sodium sulphate, filtered and concentrated under reduced pressure. The material obtained (0.31 g) was further purified by preparative thin layer chromatography (silica/diethylether) to give Compound No. 88 (0.15 g, 44%) as a white solid, m.p 165°-166° C.

EXAMPLE 43

This Example describes the preparation of Compound No. 89 in Table I.

Step A

Potassium carbonate (13.82 g) was suspended in a DMSO solution (100 $cm^3$) containing 2,4-dichlorophenol (8.15 g) and warmed to approximately 100° C. to give a grey solution. 18-Crown-6 (0.13 g) and 4-fluoroacetophenone (6.04 $cm^3$) were added. The mixture was warmed to 150° C. and stirred overnight.

After cooling to room temperature the mixture was diluted with water, extracted with diethyl ether (four times) using brine to break the emulsion Combined ether extracts were washed with 2 M sodium hydroxide solution and water, dried over anhydrous magnesium sulphate and filtered. The dark solution was decolourised twice with activated charcoal, filtered through hiflow and concentrated under reduced pressure to give 4-(2,4-dichlorophenoxy)acetophenone, (10.8 g 78%) as a yellow/brown solid.

δH NMR ($CDCl_3$): 2.55(s)3H; 6.9(d)2H; 7.05(d)1H; 7.25(dd)1H; 7.5(d)1H; 7.95(dt)2H.

Step B 4-(2,4-Dichlorophenoxy)acetophenone (0.5 g) prepared as described in Example 43 Step A, was dissolved in dry chloroform. m-Chloroperbenzoic acid (0.77 g) was added to the solution and the mixture stirred for 2 days with the flask enclosed in tin foil, during which time a white precipitate formed in the solution.

The precipitate was filtered off and washed briefly with a minimum of cold chloroform. The combined filtrate and washings were stirred vigorously with an aqueous solution of sodium metabisulphite, separated and the chloroform extract washed with aqueous potassium carbonate solution (twice) and water (twice), dried over anhydrous sodium sulphate, filtered and concentrated under reduced pressure to give a yellow oil (0.62 g).

The oil (0.3 g) was purified by preparative thin layer chromatography (silica/hexane-$Et_2O$, 10:1) 4-(2,4-dichlorophenoxy)phenylacetate as a yellow oil (0.21 g, 79%).

δH NMR($CDCl_3$):δ2.3(s)3H; 6.95(m)3H; 7.05(d)2H; 7.20(dd)1H; 7.45(d)1H.

Step C

Finely ground aluminium chloride (2.95 g) was added with gentle stirring to 4-(2,4-dichlorophenoxy)phenylacetate (4.1 g) prepared as described in Step B.

The reaction flask was plunged in to an oil bath at 90° C. The two solids formed a brown oil which was stirred, as the temperature was raised to 140° C. and held for 30 minutes. When the oil thickened and stirring became difficult, the heat was removed and the mixture allowed to cool to room temperature to give a solid brown lump.

The lump was broken down by addition of ice, concentrated hydrochloric acid and vigorous stirring. After the mixture had stood over the week-end at room temperature, a greenish white precipitate formed in the solution. The mixture was extracted with diethyl ether, washed with water, dried over anhydrous sodium sulphate, filtered and concentrated under reduced pressure to give a sticky brown solid.

The material was recrystallised from isopropanol to give 2-acetyl-4-(2,4-dichlorophenoxy)phenol (2.99 g 73%) as a yellow-brown solid m.pt 128.5°-131° C.

δH NMR $CDCl_3$: δ2.6(s)3H; 6.8(d)1H; 7.00(d)1H; 7.14(dd)2H; 7.4(d)1H; 7.5(d)1H; 12.1(s)1H.

Step D

To a suspension of sodium hydride (60% in oil) (1.53 g) in dry toluene (33 $cm^3$) warmed to reflux a solution of 2-acetyl-4-(2,4-dichlorophenoxy)phenol (4.6 g) prepared as described in Step C, in dry toluene (33 $cm^3$) was added gradually over 20 minutes. After 15 minutes a solution of diethylcarbonate (4 g) in dry toluene (33 $cm^3$) was added dropwise over 20 minutes. The mixture was then refluxed overnight and allowed to cool to room temperature, before the careful addition of water (20 cm ) with stirring to give two layers. The orange toluene layer was separated off. The aqueous extract was acidified with dilute hydrochloric acid and a cream precipitate formed which was filtered, washed with water and air dried to give 6-(2,4-dichlorophenoxy)-4-hydroxycourmarin (4.44 g 89%) as a cream solid m.p 213°-221° C. dec.

δH NMR (DMSO) 5,0(s)1H; 7.05(d)1H; 7.2(m)1H; 7.35(dd)3H; 7.7(d)1H.

Step E

Sodium metal (0.11 g) was washed with hexane and added to EtOH (10 $cm^3$) under a nitrogen atmosphere. When all the sodium had reacted, hydroxylamine hydrochloride (0.32 g) was added, giving a yellow solution, followed by 6-(2,4-dichlorophenoxy)-4-hydroxycoumarin (0.5 g), prepared as described in Step D. The mixture was refluxed for 5 hours, allowed to cool and stand at room temperature overnight. Refluxing was continued for a further 2 hours and then the solution was allowed to cool to room temperature overnight. The mixture was concentrated under reduced pressure to give a beige solid, which was dissolved in aqueous sodium bicarbonate. The aqueous solution was extracted with diethyl ether (twice) and carefully acidified with concentrated hydrochloric acid to give a milky precipitate. The mixture was extracted with diethylether (4 times), washed with water, dried with anhydrous sodium sulphate, filtered and concentrated under reduced pressure to give Compound No. 89 as a cream beige solid (0.40 g 76%), m.p 130°-136° C.

Compound No. 96 was prepared in an analogous manner using appropriate reagents and starting materials in 37% yield. The reaction mixture was resulted for 17 hours instead of the limited period described for Compound No. 89.

EXAMPLE 44

This Example describes the preparation of Compound No. 91 in Table I.

Crude acid chloride, prepared as described in Step A of Example 40 from Compound No. 1 (0.29 g) produced as described in Example 3, was dissolved in dry dichloromethane and cooled with an ice bath. Acetone oxime (0.06 g) and triethylamine (0.08 g) were added and the ice bath removed. The mixture was allowed to warm up to room temperature overnight, diluted with dichloromethane, washed with water, dilute hydrochloric acid, dilute, aqueous sodium hydroxide and brine, dried over anhydrous sodium sulphate, filtered, and concentrated under reduced pressure.

The material obtained (0.26 g) was purified by preparative thin layer chromatography (silica/hexane-ether 1) to give Compound No. 91 as a white solid (0.17 g, 51%) m.p 127° C.

EXAMPLE 45

This Example describes the preparation of Compound No. 93 in Table I.

Compound No. 1, as produced in Example 3, (0.5 g) was dissolved in dry dichloromethane (7 $cm^3$) containing glacial acetic acid (3 $cm^3$). Bromine (0.19 g) was added and mixture stirred at room temperature for 30 minutes and then heated at reflux for 3 hours. On cooling to room temperature, the reaction mixture was diluted with dichloromethane, washed with water and brine, dried over anhydrous sodium sulphate, filtered and concentrated under reduced pressure. The residue (0.48 g) was purified by preparative thin layer chromatography (silica/hexane-diethyl ether, 1:1 with a few drops of acetic acid). The material recovered from the chromatography plates (0.24 g) was the desired product contaminated with acetic acid. The crude product was dissolved in diethyl ether, and the resulting solution washed with water and brine, then dried over anhydrous sodium sulphate. The dry solution was concentrated under reduced pressure to give Compound No. 93 (0.22 g, 36%) as a white solud, m.p 174°-175° C.

EXAMPLE 46

This example describes the preparation of Compound No. 94 in Table I.

Compound No. 4, as produced in Example 5, (0.3 g) was dissolved in dry toluene. Amberlyst polymer supported dihydrogentrifluoride, 7 mmol hydrogen fluoride/gm resin, (2 g) was added and the mixture heated at reflux for 4.75 hours. After cooling the resin was removed by filtration through hiflow and washed with diethyl ether. The filtrate and washings were combined and concentrated under reduced pressure. The residue (0.21 g) was purified by preparative thin layer chromatography (silica/hexanediethyl ether, 7:3, with 4 elutions) to give the desired product, compound No. 94 (0.04 g, 13%) as the major component of a mixture with compound No. 76 (95:5) as a yellow oil.

EXAMPLE 47

This Example describes the preparation of Compound No. 97 in Table I.

Compound No. 92, produced as in Example 10, (0.37 g) was dissolved in dry THF (6 $cm^3$) under nitrogen and the solution cooled with an ethanediol/$CO_2$ bath to −40° C. A 0.5 M solution of potassium bis(trimethylsilyl)amide in toluene (2.7 $cm^3$) was added dropwise to the reaction mixture keeping the temperature below −25° C. After stirring for 1 hour at −40° C., methyl iodide (0.42 g) was added and the mixture was allowed to warm to room temperature. The reaction mixture was poured into water and extracted with diethyl ether (5 times). The ether extract was washed with water, dried over anhydrous sodium sulphate, filtered and evaporated to dryness under reduced pressure. The material obtained (0.37 g) was purified by preparative thin layer chromatography (silica/hexane-diethylether, 7:3) to give compound No. 97 (0.24 g, 59%) as a clear oil.

Compound No. 100 was prepared from compound No. 2 in an analogous manner using appropriate reagents.

EXAMPLE 48

This Example describes the preparation of Compound No. 99 in Table I.

Compound No. 1 as produced in Example 3, (0.3 g) was dissolved in dichloromethane (10 $cm^3$). The mixture was cooled with an ice bath and dimethylaminopyridine (catalytic quantity), aniline (0.08 g) and dicyclohexylcarbodiimide (0.17 g) were added. A precipitate formed. After standing at room temperature overnight, the reaction mixture was filtered through hiflow and the residue was washed with dichloromethane. The filtrate and washings were combined, concentrated under reduced pressure and redissolved in ethyl acetate. The solution was washed with 2 M aqueous sodium hydroxide, dilute hydrochloric acid, aqueous sodium bicarbonate and brine, dried over anhydrous sodium sulphate, filtered and concentrated under reduced pressure. The material obtained (0.37 g) was further purified by preparative thin layer chromatography (silica/hexane-diethyl ether, 7:3) to give Compound No. 99 (0.06 g, 17%) as a white solid m.p 186°-187° C.

EXAMPLE 49

This Example describes the preparation of Compound No. 101 in Table I.

Step A

Compound No. 14, as produced in Example 11, (0.3 g) was dissolved in thionyl chloride (10 $cm^3$) with a little heating. The reaction mixture was allowed to stand at room temperature for ¾ hour and then concentrated under reduced pressure to give the crude acid chloride which was used directly.

Step B

The crude acid chloride from Step A was dissolved in dry dichloromethane (10 $cm^3$) and the mixture was cooled with an ice bath. Acetone oxime (0.06 g) and triethylamine (0.08 g) were added to the cooled solution, which was then left at room temperature overnight. The reaction mixture was diluted with dichloromethane, washed with dilute aqueous sodium hydroxide, dilute hydrochloric acid, and brine, dried over anhydrous sodium sulphate, filtered and concentrated under reduced pressure. The residue (0.27 g) was further purified by preparative thin layer chromatography (silica/hexane-ether, 1:1) to give Compound No. 101 (0.21 g, 62%) as an off-white solid, m.p 74°-76° C.

EXAMPLE 50

This Example describes the preparation of Compound No. 102 in Table 1.

Aqueous 1.038M sodium hydroxide solution (0.36ml) was added to a solution of Compound No. 1, as produced in Example 3, (0.15 g) in ethanol (5 $cm^3$). The reaction mixture was stirred at room temperature for 2 hours and concentrated under reduced pressure. The residue was washed with diethyl/ether and dried under reduced pressure to give Compound No. 102 (0.15 g, 100%) m.pt 239°-241° C.

Compounds Nos. 103, 104, 105, 106 and 107 were prepared in an analogous manner using appropriate reagents.

EXAMPLE 51

This example describes the preparation of compound 108 in Table II.

A solution of 0.5 M potassium bis(trimethylsilyl)amide in toluene (5.28 $cm^3$) was added slowly to a solution of compound 57, as produced in Example 21, (0.24 g) in dry THF (10 $cm^3$) cooled by an ethanediol/dry ice bath. After stirring with cooling for 1 hour, a solution of methyl iodide (0.37 g) in dry THF (2.7 $cm^3$) was added and the mixture allowed to warm to room temperature overnight. The reaction mixture was poured into water, and extracted with diethylether. The ether extract was washed with brine, dried over anhydrous sodium sulphate, filtered and concentrated under reduced pressure. The residue (0.33 g) was purified by preparative thin layer chromatogrpahy (silica/hexane-ether, 7:3) and (silica/hexane-ether, 9:1, 3 elutions). Two materials were recovered from the final chromatography, compound 100 (0.03 g, 11.7%) as a colourless oil and compound 59 (0.04 g, 16.1%) again a colourless oil. The samples of both compounds were mixtures that contained approximately 5% of the other compound.

EXAMPLE 52

This Example describes the preparation of compound 109 in Table I.

Compound 1, produced as described in Example 3, (0.3 g) was dissolved in dry acetonitrile (10 $cm^3$) and the solution cooled with an ice bath. A catalytic quantity of 4-dimethylaminopyridine and dicyclohexylcarbodiimide (0.17 g) were added to the cooled solution, and a yellow precipitate was observed. After the addition of 2-aminopyridine (0.08 g), the ice bath was removed and the mixture stirred at room temperature for 2 hours. The mixture was filtered through hi-flow and the residue washed with acetonitrile. The combined washings and filtrate were concentrated under reduced pressure. The residue (0.44 g) was further purified by preparative thin layer chromatography (silica/hexane-ether, 3:7) to give compound 109 (0.35 g, 98%) as a white solid, m.pt 144°-146° C.

EXAMPLE 53

This Example describes the preparation of compound 110 in Table I.

Compound 1, produced as described in Example 3, (0.3 g) was dissolved in dry acetonitrile (10 $cm^3$) and the solution cooled with an ice bath. A catalytic quantity of 4-dimethylaminopyridine and dicyclohexylcarbodiimide (0.17 g) were added to the cold solution and precipitate observed. Following the addition of 3-aminopyridine (0.08 g) to the cold solution, a thicker precipitate was observed and the ice bath removed. After stirring at room temperature for 0.75 hours no reaction could be detected so the mixture was heated at reflux for 1.75 hours. After cooling, further portions of DCC (0.17 g) and 3-aminopyridine (0.08 g) were added to the reaction mixture which was then left at room temperature overnight. The reaction mixture was filtered and the residue washed with acetonitrile. The filtrate and washings were combined and concentrated under reduced pressure. The concentrate (0.46 g) was further purified by preparative thin layer chromatography (silica/ diethyl ether) to give compound 110 (0.06 g, 17%) as a white solid, m.pt 201°-203° C.

EXAMPLE 54

This Example describes the preparation of compound 111 Table I.

Compound 1, as produced in Example 3, (0.3 g) was dissolved in dry acetonitrile (10 $cm^3$) and the solution cooled with an ice bath. A catalytic quantity of DMAP and DCC (0.17 g) were added and a yellow precipitate was observed. Following the addition of 4-aminopyridine (0.08 g) further precipitate formed and the reaction mixture was left at room temperature overnight. Triethylamine (0.1 g) was added and the reaction mixture again left at room temperature overnight. The mixture was filtered and the residue washed with acetonitrile. The washings and filtrate were combined and concentrated under reduced pressure to give a dirty yellow solid (0.24 g). The solid was further purified by preparative thin layer chromatography (silica/diethyl ether) to give compound 111 as a white solid (0.05 g, 11%), m.pt 239° C. (decomposed).

EXAMPLE 55

This Example describes the preparation of compounds 112 and 113 in Table I.

A 0.5m solution of potassium bis(trimethylisilyl) amide in toluene (4,36 $cm^3$) was added dropwise to a solution of compound 2, produced as in Example 2, (0.8 g) in dry THF (20 $cm^3$) and cooled with a dry ice/ethanediol/isopropanol bath. The mixture was cooled and stirred for one hour at approximately −40° C. Allyl bromide (0.19 $cm^3$) in dry THF (2 $cm^3$) was added and the mixture stirred at −40° C. for one hour before being allowed to warm to room temperature. A yellow solid precipitated out of solution as the temperature rose.

The mixture was diluted with water, extracted with diethyl ether (four times), washed with water, dried with anhydrous magnesium sulphate, filtered and concentrated under reduced pressure to give a brown oil (1.0 g).

The oil obtained was purified three times by preparative thin layer chorotography (silica/hexane-ethyl acetate 2:1, 4:1 and 7:1) to give compound 112 (0.53 g 60%) as an oil and compound 113 (0.04 g, 4%) as an oil.

Compounds 114 and 115 were produced in an analogous manner using appropriate starting materials and reagents.

EXAMPLE 56

This Example illustrates the preparation of compound 116 in Table III.

Step A m-Fluoroacetophenone (20.0 g, 0.14 mol) was cooled to below −5° C. and fuming nitric acid (100 $cm^3$) added dropwise at such a rate that the temperature of the reaction mixture never exceeded −5° C. When the addition was complete the mixture was poured into ice/water. The precipitated yellow solid was filtered, washed with water and dried to give 5-fluoro-2-nitroacetophenone (21.4 g).

Step B 5-fluoro-2-nitroacetophenone (9.15 g, 50 mmol) and 4-chloro-3-hydroxy-1-methyl-5-trifluromethylpyrazole (10.03 g, 50 mmol) were heated together at 90° for 3 hours, then diluted with dimethylsulphoxide (60 $cm^3$) and potassium carbonate (5.30 g, 50 mmol) added. The reaction mixture was stirred at 100° C. for 90 minutes, cooled to room temperature and poured into ice/water. The mixture was extracted with ethyl acetate, the organic extracts were combined, dried ($MgSO_4$) and evaporated in vacuo. The residue was triturated with 60-80 petroleum ether to give 5-(4-chloro-1-methyl-5 trifluoromethyl-1H-pyrazol-3 yloxy) -2-nitroacetophenone (13.54 g) m.p. 92°-94°.

Step C

The nitroacetophenone prepared in Step B (11.0 g, 30.5 mmol) was dissolved in acetone (180 $cm^3$) and cooled to 10° C. Titanium trichloride (30% aqueous solution, 130 $cm^3$) was added dropwise over 30 minutes, and once the addition was complete the reaction mixture was allowed to warm to room temperature. The mixture was poured into water and extracted with ethyl acetate. The organic extracts were combined, washed with brine, dried (M ) filtered and the solvent removed in vacuo to afford a brown solid. Trituration with 60–80 petroleum ether gave 2-amino-5-(4-chloro-1-methyl-5-trifluoromethyl-1H-pyrazol-3-yloxy)acetophenone (10.0 g) m.p. 90°–92°.

Step D

The amine prepared in step C (10.0 g, 30.3 mmol) was suspended in water (120 $cm^3$) and acidified with concentrated hydrochloric acid. The mixture was cooled in an ice-salt bath and a solution of sodium nitrite (2.3 g, 33.3 mmol) in water (25 $cm^3$) was added dropwise and after the addition was complete the mixture was stirred at 0° C. for 20 minutes. A solution of fluoroboric acid (20 $cm^3$) was added with vigorous stirring. When the addition was complete the reaction mixture was allowed to warm to room temperature. The precipitate was collected and dried.

The solid prepared above was added to a solution of cupic nitrate trihydrate (167.9 g, 695 mmol) in water (350ml) followed by cuprous oxide (4.29 g, 29.2 mmol). The mixture was stirred at room temperature for 15 minutes, then stirred at 45° C. for 6 hours. The mixture was cooled to room temperature and extracted with dichloromethane. The organic extracts were combined, dried ($MgSO_4$), filtered and evaporated in vacuo. The residue was further purified by flash column chromatography on silica gel eluting with ethyl acetate/hexane (1:3) to give 5-(4-chloro-1-methyl-5-trifluoromethyl-1H-pyrazol-3-yloxy)-2-hydroxyaceophenone (4.4 g) as a pale yellow solid m.p. 80°–82° C.

Step E

Sodium hydride (0.65 g, 27.0 mmol) was suspended in a mixture of toluene (5 $cm^3$) and 1,2-dimethoxyethane (10 $cm^3$). The hydroxyacetophenone prepared above (3.0 g, 9.0 mmol) in 1,2-dimethoxyethane (20 $cm^3$) was added dropwise, and when the addition was complete the mixture was heated to 60° C. After one hour, diethyl carbonate (3.25 $cm^{3,\ 27.0}$ mmol) was added, and the mixture stirred under reflux for a further two hours.

The mixture was cooled to room temperature and poured into ice/water. The aqueous phase was extracted with ethyl acetate and then acidified with dilute aqueous hydrochloric acid and extracted once more with ethyl acetate. The organic extract was dried ($MgSO_4$) and the solvent removed in vacuo to afford 6-(4-chloro-1-methyl-5-trifluoromethyl-1H-pyrazol-3-yloxy)-4-hydroxycoumarin (1.95 g) as a waxy solid.

Step F

Sodium metal (0.36 g, 15.6 mmol) was dissolved in ethanol (10 $cm^3$) and hydroxylamine hydrochloride (1.07 g, 15.4 mmol) was added. The mixture was stirred for five minutes, the coumarin prepared in Step E (1.87 g, 5.2 mmol) added, and the mixture heated under reflux for 17 hours. A further quantity of hydroxylamine hychloride (1.07 g, 15.4 mmol) was added and the mixture heated under reflux for a further 3 hours. The mixture was cooled to room temperature and the solvent removed in vacuo. The residue was taken up in saturated aqueous sodium bicarbonate solution. The mixture was washed with diethyl ether, acidified with concentrated hydrochloric acid and extracted with ethyl acetate. The combined ethyl acetate extracts were washed with brine, dried ($MgSO_4$) and the solvent removed in vacuo. Trituration with 60–80 petroleum ether gave a light brown solid. Recrystallisation (ethyl acetate/hexane) gave compound No. 116 (1.27 g) m.p. 137°–138° C.

EXAMPLE 57

This Example illustrates the synthesis of compound 117 in Table III.

Compound 116, as produced in Example 56, (0.35 g, 0.93 mmol) was dissolved in methanol, two drops of concentrated sulphuric acid were added and the mixture heated under reflux for 16 hours. The mixture was cooled to room temperature and the solvent evaporated in vacuo. The residue was taken up in ethyl acetate washed with water, dried ($MgSO_4$) and the solvent removed in vacuo.

The residue was further purified by flash column chromatography on silica gel, eluting with ethyl acetate/hexane (1:2) to give Compound No. 117 (0.21 g) as a colourless solid m.p 82°–84° C.

Compound No. 118 was prepared in an analogous manner using appropriate reactants.

EXAMPLE 58

This Example illustrates the synthesis of compound 121 in Table III.

Compound 117, produced as in Example 57 (1.0 g 2.6 mmol) was dissolved in tetrahydrofuran (10 $cm^3$) and the solution cooled in an ice/salt bath. Potassium t-butoxide (0.35 g 3.2 mmol) was added and the mixture was stirred for 30 minutes. Methyl iodide (0.2$cm^3$, 3.2 mmol) was added and the mixture stirred for 2 hours and then allowed to warm to room temperature.

The reaction mixture was poured into ice/water and extracted with ethyl acetate. The organic extracts were combined, dried ($MgSO_4$) evaporated in vacuo and the residue purified by flash column chromatography on silica gel, eluting with ethyl acetate/hexane (1:3) to give compound 121 (0.57 g) as a pale yellow gum.

EXAMPLE 59

This Example illustrates the preparation of compound 120 in Table III.

Compound 121, produced in Example 58, (0.25 g, 0.62 mmol) was dissolved in a mixture of tetrahyrofuran (6$cm^3$) and water (3 $cm^3$) and potassium hydroxide (0.04 g, 0.68 mmol) added. The mixture was heated under reflux for 3 hours cooled and poured into water. The mixture was washed with diethyl ether, the aqueous phase acidified with dilute aqueous hydrochloric acid and extracted with diethyl ether. The ethereal extracts were combined, dried and the solvent evaporated in vacuo. Trituration with hexane gave compound 120 (0.16 g) as a solid m.p. 101°–103° C.

EXAMPLE 60

This Example illustrates the preparation of Compound No. 122 in Table III.

Compound 120, produced as in Example 59, (0.40 g, 1.2 mmol), 4-dimethylaminopyridine (0.19 g, 1.5 mmol) and ethanol (2 $cm^3$) were stirred together in 1,2- dichloroethane (5 $cm^3$) and the mixture cooled in an ice-bath. Dicyclohexylcarbodiimide (0.32 g, 1.5 mmol) was added and the mixture stirred for 17 hours, allowing it to warm to room temperature. The mixture was filtered through celite, the solvent evaporated and the residue purified by flash column chromatography on silica gel, eluting with ethyl acetate/hexane (1:2) to give compound 122 (0.19 g) as a pale yellow gum.

EXAMPLE 61

This Example illustrates the preparation of compound 119 in table III.

Compound 116, produced as in Example 56, (0.50 g, 1.3 mmol) was suspended in dichloromethane (1.5 $cm^3$) and oxalyl chloride (0.4 $cm^3$) and N,N-dimethylformamide (1 drop) were added. The mixture was stirred at room temperature for 17 hours, the solvent removed in vacuo, and aqueous ammonia (sp.gr 0.88) added. The mixture was stirred for a few minutes and the extracted with ethyl acetate. The organic extracts were combined, dried ($MgSO_4$) and the solvent removed in vacuo. The residue was further purified by flash column chromatography on silica gel eluting with ethyl acetate to give compound 119 (0.10 g) as a beige solid, m.p. 147°-149° C.

EXAMPLE 62

This Example describes the preparation of Compound 123 in Table I.

A suspension of compound 68, prepared as described in Example 29, (0.35 g) was suspended in toluene (10 $cm^3$) with Lawesson's Reagent (0.2 g) and the mixture heated at reflux for 1.75 hours. During the heating the suspension dissolved to give a solution. On cooling to room temperature a solid formed and the reaction mixture was poured into water and extracted with diethylether. The extract was washed with water and brine, dried over anhydrous sodium sulphate, filtered and concentrated under reduced pressure. The residue of the ether extract was further purified by preparative thin layer chromatography (silica/chloroform) to give compound 123 as a yellow solid (0.05 g, 14%) m.p. 170°-172° C.

Biological Data

The herbicidal activity of the compounds was tested as follows:

Each chemical was formulated by dissolving it in an appropriate amount, dependent on the final spray volume, of a solvent/surfactant blend, which comprised 78.2 gm/liter of Tween 20 and 21.8 gm/liter of Span 80 adjusted to 1 liter using methylcyclohexanone. Tween 20 is a Trade Mark for a surface-active agent comprising a condensate of 20 molar proportions of ethylene oxide with sorbitan laurate. Span 80 is a Trade Mark for a surface-active agent comprising sorbitan mono-laurate. If the chemical did not dissolve, the volume was made up to 5 $cm^3$ with water, glass beads were added and this mixture was then shaken to effect dissolution or suspension of the chemical, after which the beads were removed. In all cases, the mixture was then diluted with water to the required spray volume. If sprayed independently, volumes of 25 $cm^3$ and 30 $cm^3$ were required for pre-emergence and post-emergence tests respectively; if sprayed together, 45 $cm^3$ was required. The sprayed aqueous emulsion contained 4% of the initial solvent/surfactant mix and the test chemical at an appropriate concentration.

The spray compositions so prepared were sprayed onto young pot plants (post-emergence test) at a rate equivalent to 1000 liters per hectare. Damage to plants was assessed 13 days after spraying by comparison with untreated plants, on a scale of 0 to 9 where 0 is 0% damage, 1 is 1-5% damage, 2 is 6-15% damage, 3 is 16-25% damage, 4 is 26-35% damage, 5 is 36-59% damage, 6 is 60-69% damage, 7 is 70-79% damage, 8 is 80-89% damage and 9 is 90-100% damage.

In a test carried out to detect pre-emergence herbicidal activity, crop seeds were sown at 2 cm depth (i.e. Sb, Ct, Rp, Ww, Mz, Rc, Sy) and weed seeds at 1 cm depth beneath compost and sprayed with the compositions at the rate of 1000 liters per hectare. 20 days after spraying, the seedlings in the sprayed plastic trays were compared with the seedlings in unsprayed control trays, the damage being assessed on the same scale of 0 to 9.

The results of the tests are given in Table V below.

TABLE V

| COMPOUND NO. | RATE OF APPLICATION kg/ha | PRE-OR POST-EMERGENCE APPLICATION | TEST PLANTS (see Table VI) | | | | | | | | | | | | | | | | | | | | | | | |
|---|---|---|---|---|---|---|---|---|---|---|---|---|---|---|---|---|---|---|---|---|---|---|---|---|---|---|
| | | | Sh | Rp | Ct | Sy | Mz | Rc | Ww | Pi | Ca | Ga | Am | Bd | Eh | Ip | Ab | Xa | Xs | Av | Al | Ag | Sh | St | Dg | Ec | Ce |
| 1 | Pre | 1 | 9 | 9 | 0 | 0 | 0 | 7 | 0 | — | 9 | — | 9 | 9 | 9 | 7 | 9 | 0 | — | 0 | 0 | — | 9 | 9 | 9 | 6 | 0 |
| | Post | | 9 | 9 | 9 | 9 | 9 | 8 | 9 | 9 | 9 | 9 | 9 | 9 | 9 | 9 | 9 | — | 9 | 9 | 9 | 9 | 9 | 9 | 9 | 9 | 9 |
| 2 | Pre | 1 | 9 | 9 | 0 | — | 0 | — | 0 | 7 | 9 | — | 9 | 8 | 9 | 5 | 9 | 3 | — | 0 | 1 | — | — | 9 | 9 | 8 | — |
| | Post | | 9 | 9 | 9 | 9 | 9 | 9 | 9 | 9 | 9 | 9 | 9 | 9 | 9 | 9 | 9 | — | 9 | 9 | 9 | 9 | 9 | 9 | 9 | 9 | 9 |
| 3 | Pre | 1 | 8 | 8 | 5 | 2 | 0 | 3 | 2 | — | 9 | 6 | 9 | 7 | 9 | 3 | 9 | 2 | — | 5 | 9 | — | 9 | 9 | 9 | 8 | 0 |
| | Post | | 9 | 9 | 9 | 9 | 9 | — | 8 | 9 | 9 | 9 | 9 | 9 | 9 | 9 | 9 | — | 9 | 8 | 7 | 7 | 9 | 9 | 9 | 9 | 6 |
| 4 | Pre | 0.25 | 0 | 0 | 0 | — | 0 | 0 | 0 | — | 9 | 2 | 5 | 0 | 8 | 4 | 2 | 2 | — | 0 | 0 | — | 0 | 5 | 0 | 0 | — |
| | Post | | 9 | 9 | 9 | 9 | 9 | — | 9 | 9 | 9 | 9 | 9 | 9 | 9 | 9 | 9 | — | 9 | 9 | 8 | 9 | 9 | 9 | 9 | 9 | 9 |
| 5 | Pre | 0.25 | 4 | 5 | 2 | 2 | 0 | 4 | 0 | — | 9 | 7 | 9 | 3 | 9 | 5 | 7 | 0 | — | 0 | 5 | — | 7 | 7 | 9 | 3 | — |
| | Post | | 9 | 9 | 9 | 9 | 9 | — | 9 | 9 | 9 | 9 | 9 | 9 | 9 | 9 | 9 | — | 9 | 9 | 9 | 9 | 9 | 9 | 9 | 9 | 8 |
| 6 | Pre | 0.25 | 3 | 4 | 0 | 3 | 0 | 2 | 0 | — | 9 | 5 | 9 | 4 | 8 | 0 | 8 | 3 | — | 2 | 5 | — | 5 | 9 | 9 | 5 | — |
| | Post | | 9 | 9 | 9 | 9 | 9 | — | 9 | 9 | 9 | 9 | 9 | 9 | 9 | 9 | 9 | — | 9 | 9 | 9 | 9 | 9 | 9 | 9 | 9 | 9 |
| 7 | Pre | 0.25 | 4 | 2 | 5 | 5 | 0 | 5 | 0 | — | 9 | 2 | 5 | 3 | 5 | 2 | 0 | 0 | — | 2 | 2 | — | 5 | 4 | 3 | 0 | 0 |
| | Post | 0.062 | 9 | 9 | 9 | 9 | 9 | — | 7 | 9 | 9 | 9 | 9 | 9 | 9 | 9 | 9 | — | 9 | 9 | 6 | 9 | 9 | 9 | 9 | 9 | 8 |
| 8 | Pre | 1 | 9 | 9 | 6 | 6 | 0 | 6 | 5 | 9 | 9 | 3 | 9 | 9 | 9 | 5 | 9 | 5 | — | 7 | 9 | — | 5 | 9 | — | 9 | — |
| | Post | 0.064 | 9 | 9 | 9 | 7 | 6 | 5 | 6 | — | 9 | 9 | 9 | 9 | 9 | 9 | 9 | — | 9 | 9 | 7 | 7 | 9 | 9 | 9 | 9 | — |
| 9 | Pre | 1 | 9 | 9 | 5 | 0 | 0 | 5 | 0 | 9 | 9 | 2 | 9 | 8 | 9 | 5 | 9 | 4 | — | 7 | 7 | — | 5 | 9 | — | 9 | — |
| | Post | 0.064 | 7 | 9 | 9 | 9 | 9 | 4 | 5 | — | 9 | 9 | 9 | 9 | 9 | 9 | 9 | — | 9 | 6 | 6 | 6 | 9 | 9 | 9 | 9 | — |
| 10 | 0.25 | Pre | — | — | 0 | 0 | 0 | 0 | 0 | 5 | 9 | — | 9 | 5 | 7 | 4 | 5 | 0 | — | 0 | 0 | — | 2 | 5 | 6 | 4 | — |
| | 0.0625 | Post | 9 | 9 | 9 | 9 | 6 | 4 | 5 | 9 | 9 | 9 | 9 | 9 | 9 | 9 | 9 | — | 9 | 6 | 9 | 5 | 9 | 9 | 9 | 6 | 5 |
| 11 | 0.25 | Pre | 5 | — | 2 | 0 | 3 | 5 | 4 | 5 | 9 | — | 8 | 4 | 3 | 2 | 4 | 0 | — | 0 | 4 | — | 0 | 4 | 5 | 3 | — |
| | 0.0625 | Post | 9 | 9 | 9 | 9 | 7 | 5 | 5 | 9 | 9 | 9 | 9 | 9 | 9 | 9 | 9 | — | 9 | 5 | 7 | 5 | 9 | 9 | 9 | 6 | 5 |
| 12 | | Pre | 5 | — | — | 0 | 0 | 6 | 0 | 5 | 9 | — | 8 | 4 | 6 | 0 | 5 | 0 | — | 0 | 2 | — | — | 6 | 2 | 6 | — |
| | 0,25 | Post | 9 | 9 | 9 | 9 | 9 | 5 | 6 | 9 | 9 | 9 | 9 | 9 | 9 | 9 | 9 | — | 9 | 7 | 8 | 5 | 9 | 9 | 9 | 9 | 7 |
| 13 | 0.25 | Pre | — | — | 2 | 3 | 0 | 4 | 0 | 5 | 9 | — | 8 | 5 | 8 | 5 | 6 | 4 | — | 0 | 3 | — | 5 | 6 | 6 | 5 | — |
| | 0.0625 | Post | 9 | 9 | 9 | 9 | 6 | 5 | 6 | 9 | 9 | 9 | 9 | 9 | 9 | 9 | 9 | — | 9 | 7 | 7 | 4 | 8 | 9 | 9 | 6 | 4 |
| 14 | 0.25 | Pre | 4 | 7 | 0 | 2 | 0 | 9 | 0 | 9 | 9 | — | 9 | 1 | 9 | 3 | 9 | 0 | — | 0 | 0 | — | 2 | 8 | 7 | 0 | — |
| | 0.0625 | Post | 9 | 9 | 9 | 7 | 5 | 3 | 3 | 9 | 9 | 8 | 9 | 9 | 9 | 9 | 9 | — | 9 | 4 | 4 | 5 | 7 | 5 | 7 | 6 | — |
| 15 | 0.25 | Pre | 7 | 9 | 0 | 0 | 0 | 8 | 0 | 7 | 9 | — | 9 | 2 | 8 | 5 | 9 | 0 | — | 2 | 0 | — | 2 | 7 | 7 | 0 | — |
| | 0.0625 | Post | 9 | 9 | 9 | 7 | 6 | 4 | 3 | 9 | 9 | 8 | 9 | 6 | 9 | 9 | 9 | — | 9 | 5 | 3 | 4 | 8 | 5 | 8 | 5 | — |
| 16 | 0.25 | Pre | 6 | 9 | 0 | 0 | 2 | 6 | 0 | 9 | 9 | 0 | 9 | 5 | 8 | 0 | 9 | 0 | — | 2 | 0 | — | 0 | 8 | 7 | 0 | — |
| | 0.0625 | Post | 9 | 9 | 9 | 6 | 6 | 4 | 4 | 9 | 9 | 9 | 9 | 9 | 9 | 9 | 9 | — | 9 | 5 | 3 | 3 | 8 | 6 | 9 | 6 | — |
| 17 | 0.25 | Pre | 4 | 6 | 3 | 0 | 0 | 8 | 3 | 9 | 9 | — | 9 | 3 | 8 | 3 | 9 | 0 | — | 2 | 0 | — | 2 | 5 | 6 | 0 | — |
| | 0.0625 | Post | 9 | 9 | 9 | 9 | 8 | 4 | 4 | 9 | 9 | 9 | 9 | 9 | 9 | 9 | 9 | — | 9 | 5 | 5 | 4 | 8 | 5 | 9 | 6 | — |
| 18 | 0.15 | Pre | 8 | 8 | 0 | 0 | 0 | 9 | 0 | 9 | 9 | — | 9 | 5 | 7 | 4 | 9 | 0 | — | 0 | 1 | — | 0 | 7 | 5 | 0 | — |
| | 0.0625 | Post | 9 | 9 | 9 | 7 | 8 | 4 | 4 | 9 | 9 | 9 | 9 | 9 | 9 | 9 | 9 | — | 9 | 6 | 6 | 4 | 9 | 5 | 9 | 6 | — |
| 19 | 0.25 | Pre | 9 | 8 | 0 | 0 | 2 | 7 | 3 | 9 | 9 | — | 9 | 8 | 9 | 6 | 8 | 0 | — | 3 | 5 | — | 3 | 9 | 9 | 3 | 0 |
| | 0.016 | Post | 9 | 9 | 9 | 8 | 5 | 4 | 5 | 9 | 9 | 9 | 9 | 9 | 9 | 8 | 9 | — | 9 | 7 | 7 | 4 | 9 | 8 | 9 | 3 | — |
| 20 | 0.25 | Pre | 9 | 9 | 2 | 3 | 2 | 7 | 7 | 6 | 9 | — | 9 | 9 | 9 | 4 | 7 | 3 | — | 2 | 4 | — | 7 | 7 | 9 | 6 | 0 |
| | 0.016 | post | 5 | 8 | 9 | 7 | 6 | 3 | 4 | 9 | 9 | 8 | 9 | 5 | 9 | 8 | 5 | — | 9 | 5 | 5 | 2 | 6 | 7 | 6 | 4 | — |
| 21 | 0.25 | Pre | 8 | 9 | 4 | 3 | 2 | 8 | 3 | 9 | 9 | — | 9 | 7 | 9 | 2 | 8 | 2 | — | 3 | 3 | — | 5 | 7 | 9 | 2 | 2 |
| | 0.016 | Post | 9 | 7 | 9 | 6 | 5 | 3 | 6 | 9 | 9 | 9 | 9 | 9 | 9 | 8 | 9 | — | 9 | 5 | 6 | 4 | 9 | 9 | 9 | 8 | — |
| 22 | 0.25 | Pre | 9 | 3 | 3 | 3 | 2 | 0 | 0 | 3 | 9 | — | 9 | 7 | 8 | 2 | 4 | 2 | — | 0 | 2 | — | 0 | 4 | 7 | 0 | 0 |
| | 0.016 | Post | 9 | 7 | 9 | 5 | 6 | 3 | 5 | 9 | 9 | 9 | 9 | 6 | 9 | 6 | 9 | — | 8 | 5 | 6 | 4 | 9 | 7 | 7 | 6 | — |
| 24 | 0.016 | Post | 9 | 9 | 9 | 7 | 6 | 3 | 5 | 9 | 9 | 9 | 9 | 6 | 8 | 8 | 9 | — | 9 | 6 | 5 | 3 | 9 | 8 | 8 | 6 | — |
| 25 | 0.25 | Pre | 7 | 9 | 0 | 0 | 3 | 5 | 4 | 9 | 9 | — | 7 | 5 | 9 | 4 | 5 | 0 | — | 2 | 3 | — | 0 | 2 | 7 | 2 | 0 |
| | 0.016 | Post | 8 | 8 | 9 | 5 | 5 | 4 | 4 | 9 | 9 | 9 | 9 | 8 | 9 | 9 | 9 | — | 7 | 6 | 5 | 3 | 9 | 6 | 9 | 5 | — |
| 26 | 0.25 | Pre | 9 | 9 | 2 | 0 | 0 | 7 | 2 | 9 | 9 | — | 9 | 6 | 9 | 0 | 9 | 4 | — | 5 | 3 | — | 5 | 6 | 4 | 3 | 9 |
| | 0.0625 | Post | 9 | 9 | 9 | 5 | 7 | 2 | 4 | 9 | 9 | 9 | 9 | 9 | 9 | 9 | 9 | — | 9 | 7 | 2 | 6 | 6 | 9 | 9 | 9 | 7 |
| 27 | 0.25 | Pre | 9 | 9 | 3 | 4 | 0 | 2 | 0 | 9 | 9 | — | 9 | 6 | 9 | 4 | 9 | 2 | — | 6 | 5 | — | 3 | 9 | 4 | 3 | 0 |

TABLE V-continued

| COMPOUND | RATE OF APPLICATION | PRE-OR POST-EMERGENCE | TEST PLANTS (see Table VI) | | | | | | | | | | | | | | | | | | | | | | | |
|---|---|---|---|---|---|---|---|---|---|---|---|---|---|---|---|---|---|---|---|---|---|---|---|---|---|---|
| NO. | kg/ha | APPLICATION | Sb | Rp | Ct | Sy | Mz | Rc | Ww | Pi | Ca | Ga | Am | Bd | Eh | Ip | Ab | Xa | Xs | Av | Al | Ag | Sh | St | Dg | Ec | Ce |
| | 0.0625 | Post | 7 | 9 | 9 | 5 | 6 | 3 | 3 | 9 | 9 | 9 | 9 | 9 | 9 | 9 | 9 | — | 9 | 3 | 2 | 4 | 7 | 7 | 6 | 2 | 5 |
| 29 | 0.25 | Pre | 9 | 9 | 3 | 3 | 4 | 0 | 0 | 9 | 9 | — | 9 | 5 | 3 | 0 | 9 | 0 | — | 0 | 0 | — | 0 | 8 | 9 | 0 | 0 |
| | 0.0625 | Post | 7 | 9 | 9 | 9 | 8 | 8 | 6 | 9 | 9 | — | 9 | 8 | 9 | 9 | 9 | — | 9 | 9 | 6 | 4 | 9 | 9 | 9 | 4 | — |
| 30 | 0.25 | Pre | 9 | 9 | 3 | 5 | 0 | 3 | 0 | 9 | 9 | — | 9 | 7 | 9 | 0 | 9 | 0 | — | 0 | 0 | — | 0 | 9 | 9 | 0 | 0 |
| | 0.0625 | Post | 9 | 9 | 9 | 8 | 8 | 5 | 6 | 9 | 9 | — | 9 | 9 | 9 | 8 | 9 | — | 9 | 9 | 6 | 9 | 9 | 9 | 9 | 7 | — |
| 31 | 0.25 | Pre | 9 | 5 | 5 | 5 | 4 | 0 | 0 | 9 | 9 | — | 9 | 5 | 9 | 6 | 9 | 4 | — | 3 | 0 | — | 0 | 9 | 9 | 0 | 7 |
| | 0.0625 | Post | 9 | 9 | 9 | 8 | 9 | 6 | 9 | 9 | 9 | — | 9 | 9 | 9 | 9 | 9 | — | 9 | 9 | 9 | 9 | 9 | 9 | 9 | 6 | — |
| 32 | 0.25 | Pre | 9 | 9 | 3 | 5 | 0 | 0 | 4 | 9 | 9 | — | 9 | 7 | 9 | 3 | 9 | 4 | — | 5 | 0 | — | 0 | 9 | 9 | 0 | 4 |
| | 0.0625 | Post | 9 | 9 | 9 | 9 | 6 | 5 | 9 | 9 | 9 | — | 9 | 9 | 9 | 9 | 9 | — | 9 | 9 | 9 | 6 | 9 | 9 | 9 | 9 | — |
| 33 | 1 | Pre | 0 | 0 | 0 | 0 | 0 | 0 | 0 | 0 | 7 | — | 0 | 0 | 8 | 0 | 0 | 0 | — | 0 | 0 | — | 1 | 5 | 0 | 6 | 0 |
| | 0.25 | Post | 7 | 9 | 9 | 9 | 8 | 0 | 8 | 9 | 9 | — | 9 | 5 | 7 | 9 | 7 | — | 7 | 5 | 3 | 7 | 9 | — | 3 | 9 | 2 |
| 34 | 1 | Pre | 5 | 6 | 0 | 0 | 0 | 3 | 0 | 5 | 9 | — | 6 | 0 | 8 | 0 | 6 | 0 | — | 0 | 0 | — | 0 | 0 | 0 | 9 | 0 |
| | 0.25 | Post | 7 | 9 | 9 | 9 | 7 | 3 | 9 | 9 | 9 | — | 9 | 7 | 9 | 8 | 9 | — | 6 | 5 | 2 | 9 | 9 | — | 0 | 9 | 2 |
| 35 | 1 | Pre | 2 | 5 | 0 | 0 | 0 | 0 | 0 | 0 | 0 | — | 0 | 0 | 0 | 0 | 0 | 0 | — | 0 | 0 | — | 0 | 0 | 0 | 0 | 0 |
| | 0.25 | Post | 9 | 8 | 6 | 2 | 4 | 1 | 3 | 9 | 9 | — | 9 | 6 | 3 | 3 | 9 | — | 2 | 2 | 0 | 0 | 2 | — | 0 | 6 | 0 |
| 36 | 1 | Pre | 0 | 4 | 0 | 0 | 0 | 0 | 0 | 0 | 4 | — | 4 | 0 | 6 | 0 | 0 | 0 | — | 0 | 0 | — | 2 | 0 | 0 | 5 | 0 |
| | 0.25 | Post | 5 | 8 | 8 | 7 | 5 | 0 | 8 | 9 | 9 | — | 8 | 5 | 9 | 5 | 2 | — | 5 | 5 | 2 | 1 | 6 | — | 2 | 6 | 0 |
| 37 | 1 | Pre | 0 | 7 | 0 | 0 | 0 | — | 0 | 0 | 3 | — | 0 | 0 | 5 | 0 | 0 | 0 | — | 0 | 0 | — | 3 | 5 | 0 | 8 | 0 |
| | 0.25 | Post | 5 | 9 | 9 | 9 | 8 | 0 | 8 | 9 | 9 | — | 9 | 7 | 9 | 9 | 5 | — | 5 | 6 | 1 | 7 | 9 | — | 5 | 9 | 0 |
| 38 | 1 | Pre | 0 | 3 | 0 | 0 | 3 | 0 | 0 | 9 | 9 | — | 7 | 0 | 8 | 0 | 4 | 0 | — | 0 | 0 | — | 2 | 2 | 0 | 9 | 0 |
| | 0.25 | Post | 9 | 9 | 9 | 5 | 5 | 4 | 9 | 9 | 9 | — | 9 | 5 | 5 | 6 | 9 | — | 3 | 0 | 1 | 3 | 7 | — | 0 | 8 | 0 |
| 39 | 1 | Pre | 2 | 2 | 0 | 0 | 0 | 0 | 0 | 9 | 9 | — | 6 | 0 | 7 | 0 | 1 | 2 | — | 0 | 0 | — | 1 | 2 | 1 | 9 | 0 |
| | 0.25 | Post | 9 | 9 | 9 | 9 | 6 | 3 | 9 | 9 | 9 | — | 9 | 7 | 9 | 6 | 9 | — | 8 | 5 | 4 | 6 | 9 | — | 1 | 9 | 0 |
| 40 | 0.25 | Pre | 9 | 9 | 2 | 2 | 0 | 4 | 0 | 6 | 9 | — | 9 | 5 | 9 | 2 | 8 | 0 | — | 0 | 3 | — | 3 | 5 | 5 | 0 | 2 |
| | 0.0625 | Post | 9 | 9 | 9 | 9 | 7 | 4 | 5 | 9 | 9 | — | 9 | 9 | 9 | 9 | 9 | — | 9 | 3 | 4 | 5 | 9 | 9 | 9 | 8 | 4 |
| 41 | 0.25 | Pre | 8 | 9 | 3 | 3 | 2 | 3 | 5 | 9 | 9 | — | 9 | 5 | 9 | 2 | 9 | 0 | — | 0 | 0 | — | 0 | 6 | 5 | 3 | 0 |
| | 0.0625 | Post | 9 | 9 | 9 | 6 | 6 | 3 | — | 9 | 9 | — | 9 | 9 | 9 | 9 | 9 | — | 9 | 8 | 3 | 7 | 5 | 9 | 9 | 8 | 2 |
| 42 | 0.25 | Pre | 0 | 0 | 2 | 3 | 0 | 0 | 0 | 5 | 9 | — | 6 | 0 | 4 | 2 | 2 | 8 | — | 0 | 0 | — | 0 | 0 | 2 | 0 | 0 |
| | 0.0625 | Post | 6 | 9 | 9 | 9 | 6 | 3 | 4 | 9 | 9 | 9 | 9 | 9 | 9 | 9 | 9 | — | 9 | 5 | 4 | 4 | 9 | 6 | 4 | 5 | 5 |
| 43 | 0.25 | Pre | 0 | 0 | 0 | 5 | 0 | 0 | 0 | 2 | 4 | — | 3 | 0 | 2 | 0 | 2 | 0 | — | 0 | 0 | — | 0 | 0 | 3 | 0 | 0 |
| | 0.0625 | Post | 4 | 9 | 9 | 6 | 5 | 3 | 3 | 9 | 9 | 4 | 9 | 9 | 9 | 9 | 6 | — | 6 | 5 | 3 | 0 | 5 | 6 | 4 | 5 | 3 |
| 44 | 0.25 | Pre | 5 | 5 | 3 | 2 | 0 | 0 | 0 | 8 | 9 | — | 7 | 0 | 5 | 2 | 2 | 3 | — | 0 | 0 | — | 0 | 0 | 0 | 2 | 0 |
| | 0.0625 | Post | 4 | 9 | 9 | 9 | 6 | 4 | 5 | 9 | 9 | 9 | 9 | 9 | 9 | 9 | 9 | — | 9 | 3 | 5 | 5 | 7 | 7 | 5 | 7 | 4 |
| 45 | 0.25 | Pre | 0 | 0 | 0 | 0 | 0 | 0 | 0 | 2 | 3 | — | 5 | 0 | 5 | 2 | 2 | 5 | — | 0 | 0 | — | 2 | 0 | 3 | 0 | 0 |
| | 0.0625 | Post | 4 | 9 | 9 | 3 | 5 | 3 | 4 | 9 | 9 | 7 | 9 | 5 | 9 | 5 | 9 | — | 6 | 3 | 3 | 0 | 5 | 6 | 2 | 4 | 4 |
| 46 | 0.25 | Pre | 3 | 4 | 2 | 3 | 0 | 0 | 0 | 2 | 6 | — | 3 | 5 | 4 | 2 | 0 | 0 | — | 0 | 0 | — | 2 | 0 | 3 | 0 | 0 |
| | 0.0625 | Post | 5 | 9 | 9 | 8 | 5 | 4 | 4 | 9 | 9 | 9 | 9 | 9 | 9 | 9 | 9 | — | 9 | 3 | 4 | 2 | 9 | 9 | 6 | 5 | 4 |
| 47 | 0.25 | Pre | 3 | 5 | 2 | 3 | 0 | 2 | 2 | 6 | 9 | — | 8 | 0 | 5 | 0 | 5 | 0 | — | 0 | 0 | — | 0 | 0 | 0 | 0 | 0 |
| | 0.0625 | Post | 5 | 9 | 9 | 7 | 7 | 3 | 4 | 9 | 9 | 6 | 9 | 9 | 9 | 6 | 6 | — | 9 | 4 | 4 | 4 | 7 | 6 | 5 | 5 | 4 |
| 48 | 1 | Pre | 0 | 0 | 0 | 0 | 4 | 3 | 0 | 9 | 9 | — | 9 | 0 | 9 | 0 | 2 | 0 | — | 0 | 0 | — | 0 | 6 | 9 | 0 | 0 |
| | 0.25 | Post | 9 | 9 | 9 | 9 | 7 | 4 | 7 | 9 | 9 | 9 | 9 | 9 | 9 | 9 | 9 | — | 9 | 4 | 7 | 5 | 9 | 5 | 5 | 8 | 4 |
| 49 | 1 | Pre | 3 | 2 | 0 | 0 | 0 | 6 | 0 | 9 | 9 | — | 9 | 3 | 9 | 0 | 9 | 5 | — | 0 | 0 | — | 2 | 9 | 9 | 5 | 0 |
| | 0.25 | Post | 9 | 9 | 9 | 9 | 8 | 5 | 9 | 9 | 9 | 9 | 9 | 9 | 9 | 9 | 9 | — | 9 | 7 | 6 | 6 | 9 | 9 | 9 | 8 | 3 |
| 50 | 1 | Pre | 0 | 0 | 0 | 0 | 0 | 3 | 0 | 9 | 9 | — | 9 | 0 | 5 | 0 | 4 | 5 | — | 0 | 0 | — | 0 | 9 | 8 | 0 | 0 |
| | 0.25 | Post | 9 | 9 | 9 | 9 | 7 | 4 | 4 | 9 | 9 | 8 | 9 | 7 | 9 | 9 | 6 | — | 8 | 5 | 5 | 4 | 8 | 5 | 8 | 7 | 3 |
| 51 | 1 | Pre | 2 | 3 | 0 | 0 | 0 | 4 | 0 | 9 | 9 | — | 9 | 0 | 0 | 0 | 4 | 7 | — | 0 | 0 | — | 0 | 6 | 9 | 2 | 0 |
| | 0.25 | Post | 9 | 9 | 9 | 9 | 9 | 5 | 6 | 9 | 9 | 9 | 9 | 9 | 9 | 9 | 9 | — | 9 | 7 | 8 | 5 | 9 | 5 | 9 | 8 | 5 |
| 52 | 1 | Pre | 2 | 5 | 5 | 3 | 0 | 6 | 0 | 9 | 9 | — | 9 | 5 | 9 | 0 | 5 | 0 | — | 0 | 0 | — | 3 | 9 | 9 | 3 | 2 |
| | 0.25 | Post | 6 | 9 | 9 | 8 | 5 | 5 | 7 | 9 | 9 | 8 | 9 | 9 | 9 | 9 | 9 | — | 8 | 3 | 6 | 5 | 7 | 7 | 7 | 7 | 3 |
| 53 | 1 | Pre | 5 | 5 | 3 | 5 | 3 | 8 | 0 | 9 | 9 | — | 9 | 4 | 7 | 0 | 8 | 7 | — | 0 | 3 | — | 2 | 6 | 9 | 0 | 2 |

TABLE V-continued

| COMPOUND NO. | RATE OF APPLICATION kg/ha | PRE-OR POST-EMERGENCE APPLICATION | TEST PLANTS (see Table VI) | | | | | | | | | | | | | | | | | | | | | | | | |
|---|---|---|---|---|---|---|---|---|---|---|---|---|---|---|---|---|---|---|---|---|---|---|---|---|---|---|---|
| | | | Sh | Rp | Ct | Sy | Mz | Rc | Ww | Pi | Ca | Ga | Am | Bd | Eh | Ip | Ab | Xa | Xs | Av | Al | Ag | Sh | St | Dg | Ec | Cc |
| | 0.25 | Post | 9 | 9 | 9 | 9 | 8 | 5 | 8 | 9 | 9 | 9 | 9 | 9 | 9 | 9 | 9 | — | 9 | 8 | 8 | 5 | 9 | 9 | 6 | 8 | 2 |
| 54 | 1 | Pre | 3 | 8 | 0 | 0 | 2 | 0 | 0 | 5 | 9 | — | 5 | 5 | 9 | 2 | 4 | 4 | — | 2 | 3 | — | 4 | 5 | 4 | 2 | 0 |
| | 0.25 | Post | 8 | 9 | 9 | 9 | 5 | 5 | 7 | 9 | 9 | 6 | 9 | 9 | 9 | 9 | 7 | — | 9 | 4 | 7 | 9 | 9 | 9 | 8 | 9 | 3 |
| 55 | 1 | Pre | 9 | 6 | 0 | 4 | 5 | 3 | 6 | 3 | 9 | — | 9 | 2 | 9 | 2 | 3 | 0 | — | 0 | 0 | — | 4 | 0 | 7 | 0 | 0 |
| | 0.25 | Post | 5 | 9 | 9 | 9 | 6 | 5 | 5 | 9 | 9 | 5 | 9 | 7 | 9 | 9 | 4 | — | 6 | 4 | 5 | 5 | 9 | 9 | 4 | 8 | 4 |
| 56 | 1 | Pre | 9 | 8 | 0 | 2 | 0 | 6 | 0 | 9 | 9 | — | 9 | 5 | 9 | 3 | 8 | 3 | — | 3 | 5 | — | 3 | 9 | 5 | 3 | 0 |
| | 0.25 | Post | 9 | 9 | 9 | 9 | 7 | 9 | 9 | 9 | 9 | 7 | 9 | 9 | 9 | 9 | 9 | — | 9 | 6 | 6 | 9 | 9 | 9 | 8 | 9 | 4 |
| 57 | 1 | Pre | 3 | 5 | 0 | 0 | 0 | 0 | 0 | 0 | 9 | — | 6 | 5 | 9 | 0 | 0 | 0 | — | 0 | 3 | — | 4 | 5 | 5 | 0 | 0 |
| | 0.25 | Post | 9 | 9 | 9 | 9 | 6 | 5 | 9 | 9 | 9 | 9 | 9 | 9 | 9 | 9 | 9 | — | 9 | 4 | 7 | 5 | 9 | 9 | 5 | 9 | 0 |
| 58 | 1 | Pre | 9 | 9 | 0 | 5 | 0 | 0 | 0 | 9 | 9 | — | 9 | 7 | 9 | 0 | 7 | 3 | — | 0 | 0 | — | 0 | 8 | 5 | 4 | 0 |
| | 0.25 | Post | 5 | 9 | 7 | 6 | 6 | 5 | 9 | 9 | 9 | 5 | 9 | 9 | 9 | 9 | 8 | — | 9 | 5 | 6 | 8 | 7 | 9 | 7 | 9 | 5 |
| 59 | 1 | Pre | 9 | 6 | 0 | 0 | 0 | 0 | 0 | 9 | 9 | — | 9 | 3 | 9 | 0 | 9 | 3 | — | 0 | 0 | — | 0 | 9 | 9 | 0 | 0 |
| | 0.25 | Post | 8 | 9 | 9 | 9 | — | 9 | 9 | 9 | 9 | 6 | 9 | 9 | 8 | 9 | 9 | — | 9 | 8 | 6 | 9 | 9 | 9 | 6 | 9 | 5 |
| 60 | 1 | Pre | 0 | 0 | 0 | 0 | 0 | 0 | 0 | — | 8 | — | 5 | 3 | 6 | 0 | 0 | 0 | — | 0 | 1 | — | 0 | 0 | — | 0 | 0 |
| | 0.25 | Post | 5 | 6 | 6 | 5 | 5 | 1 | 0 | 9 | 9 | — | 9 | 3 | 6 | 9 | 9 | — | 5 | 2 | 3 | 0 | 8 | 7 | 4 | 5 | 3 |
| 61 | 1 | Pre | 0 | 0 | 0 | 0 | 0 | 0 | 0 | — | 7 | — | 0 | 0 | 0 | 0 | 0 | 0 | — | 0 | 0 | — | 0 | 0 | 0 | 0 | 0 |
| | 0.25 | Post | 3 | 3 | 5 | 3 | 5 | 2 | 2 | 9 | 9 | — | 9 | 2 | 3 | 1 | 2 | — | 2 | 3 | 2 | 0 | 7 | 5 | 3 | 2 | 2 |
| 62 | 1 | Pre | 0 | 0 | 0 | 0 | 0 | 0 | 0 | — | 9 | — | 9 | 6 | 5 | 0 | 5 | 0 | — | 0 | 0 | — | 0 | 0 | 0 | 0 | 0 |
| | 0.25 | Post | 9 | 8 | 9 | 4 | 5 | 2 | 3 | 9 | 9 | — | 9 | 7 | 9 | 9 | 9 | — | 6 | 7 | 2 | 5 | 9 | 8 | 2 | 6 | 2 |
| 63 | | Pre | 7 | 6 | 0 | 0 | 0 | 0 | 0 | — | 9 | — | 9 | 2 | 8 | 0 | 6 | 0 | — | 0 | 0 | — | 0 | 9 | — | 0 | 0 |
| | 0.25 | Post | 9 | 5 | 9 | 9 | 6 | 3 | 5 | 9 | 9 | — | 9 | 9 | 9 | 9 | 9 | — | 9 | 2 | 2 | 7 | 8 | 8 | 3 | 1 | 4 |
| 64 | 0.23 | Post | 9 | 9 | 9 | 7 | 7 | 5 | 2 | 9 | 9 | — | 9 | 9 | 9 | 9 | 9 | — | 9 | 8 | 5 | 3 | 9 | 9 | 3 | 0 | 3 |
| 65 | 0.25 | Pre | 6 | 5 | 2 | 6 | 0 | 0 | 0 | 9 | 9 | — | 9 | 5 | 0 | 0 | 9 | 0 | — | 0 | 4 | — | 0 | 5 | 8 | 0 | 0 |
| | 0.0625 | Post | 9 | 9 | 9 | 8 | 7 | 4 | 4 | 9 | 9 | 9 | 9 | 9 | 9 | 9 | 9 | — | 9 | 4 | 3 | 6 | 9 | 9 | 8 | 8 | 5 |
| 66 | 1 | Pre | 9 | 8 | 1 | 1 | 5 | 0 | 0 | — | 9 | — | 9 | 2 | 6 | 0 | 9 | 0 | — | 0 | 0 | — | 5 | 9 | — | 0 | 0 |
| | 0.25 | Post | 9 | 3 | 9 | 7 | 2 | 4 | 5 | 9 | 9 | — | 9 | 5 | 9 | 9 | 9 | — | 7 | 4 | 2 | 4 | 7 | 7 | 3 | 0 | 2 |
| 67 | 1 | Pre | 9 | 9 | 0 | 0 | 2 | 0 | 0 | — | 9 | — | 9 | 9 | 9 | 4 | 9 | 1 | — | 9 | 7 | — | 2 | 9 | — | 7 | 0 |
| | 0.25 | Post | 9 | 8 | 9 | 9 | 9 | 3 | 3 | 9 | 9 | — | 9 | 9 | 9 | 9 | 9 | — | 9 | 5 | 3 | 7 | 8 | 8 | 7 | 0 | 3 |
| 68 | 1 | Pre | 0 | 0 | 0 | 0 | 0 | 0 | 0 | — | 9 | — | 9 | 5 | 8 | 0 | 0 | 2 | — | 2 | 0 | — | 0 | 2 | 0 | 0 | 0 |
| | 0.0625 | Post | 9 | 9 | 9 | 6 | 2 | 4 | 3 | 9 | 9 | — | 9 | 9 | 9 | 9 | 9 | — | 9 | 3 | 3 | 7 | 9 | 9 | 9 | 0 | 4 |
| 69 | 0.25 | Pre | 9 | 9 | 0 | 0 | 0 | 0 | 0 | 9 | 9 | — | 9 | 9 | 9 | 0 | 9 | 0 | — | 3 | 0 | — | 0 | 9 | 9 | 0 | 0 |
| | 0.0625 | Post | 9 | 9 | 9 | 9 | 8 | 5 | 5 | 9 | 9 | 9 | 9 | 9 | 9 | 9 | 9 | — | 9 | 4 | 3 | 7 | 7 | 5 | 9 | 5 | 2 |
| 70 | 0.25 | Pre | 6 | 9 | 0 | 0 | 0 | 0 | 0 | 9 | 9 | — | 9 | 6 | 9 | 0 | 6 | 0 | — | 0 | 0 | — | 4 | 3 | 9 | 0 | 0 |
| | 0.0625 | Post | 9 | 9 | 9 | 9 | 9 | 4 | 6 | 9 | 9 | 9 | 9 | 9 | 9 | 9 | 9 | — | 9 | 4 | 0 | 6 | 5 | 7 | 9 | 6 | 4 |
| 71 | 0.25 | Pre | 0 | 5 | 0 | 0 | 0 | 0 | 0 | 0 | 0 | — | 3 | 5 | 0 | 0 | 0 | 0 | — | 0 | 5 | — | 0 | 0 | 7 | 0 | 0 |
| | 0.0625 | Post | 5 | 9 | 7 | 8 | 2 | 0 | 0 | 8 | 8 | 0 | 4 | 3 | 3 | 0 | 3 | — | 3 | 4 | 0 | 0 | 2 | 4 | 3 | 2 | 0 |
| 72 | 0.25 | Pre | 2 | 7 | 0 | 0 | 0 | 0 | 2 | 9 | 9 | — | 9 | 5 | 4 | 0 | 6 | 3 | — | 0 | 3 | — | 0 | 0 | 9 | 0 | 0 |
| | 0.0625 | Post | 9 | 9 | 9 | 9 | 8 | 5 | 6 | 9 | 9 | 9 | 9 | 9 | 9 | 9 | 9 | — | 9 | 7 | 6 | 6 | 7 | 5 | 9 | 5 | 4 |
| 73 | 0.25 | Pre | 5 | 7 | 0 | 4 | 0 | 0 | 4 | 0 | 8 | — | 5 | 0 | 0 | 0 | 0 | 4 | — | 0 | 0 | — | 0 | 0 | 9 | 0 | 0 |
| | 0.0625 | Post | 9 | 9 | 9 | 9 | 8 | 5 | 7 | 9 | 9 | 9 | 9 | 9 | 9 | 9 | 9 | — | 9 | 8 | 5 | 8 | 8 | 5 | 9 | 5 | 4 |
| 74 | 0.25 | Pre | 5 | 9 | 0 | 0 | 0 | 0 | 5 | 9 | 9 | — | 9 | 6 | 6 | 0 | 9 | 9 | — | 3 | 4 | — | 0 | 5 | 9 | 0 | 0 |
| | 0.0625 | Post | 9 | 9 | 9 | 9 | 8 | 4 | 5 | 9 | 9 | 9 | 9 | 9 | 9 | 9 | 9 | — | 9 | 8 | 5 | 8 | 6 | 8 | 9 | 5 | 3 |
| 75 | 0.25 | Pre | 5 | 6 | 0 | 0 | 0 | 5 | 5 | 9 | 9 | — | 8 | 4 | 5 | 9 | 5 | 0 | — | 5 | 3 | — | 0 | 0 | 9 | 0 | 0 |
| | 0.0625 | Post | 9 | 9 | 9 | 9 | 6 | 7 | 7 | 9 | 9 | 9 | 9 | 9 | 9 | 9 | 9 | — | 9 | 7 | 6 | 8 | 8 | 9 | 9 | 6 | 4 |
| 76 | 0.25 | Pre | 2 | 5 | 0 | 0 | 4 | 0 | 6 | 5 | 9 | — | 9 | 4 | 0 | 2 | 5 | 4 | — | 2 | 5 | — | 0 | 0 | 0 | 0 | 0 |
| | 0.0625 | Post | 9 | 9 | 9 | 9 | 7 | 6 | 4 | 9 | 9 | 9 | 9 | 9 | 9 | 9 | 9 | — | 9 | 8 | 6 | 4 | 9 | 9 | 9 | 6 | 5 |
| 77 | 1 | Pre | 0 | 0 | 0 | 0 | 0 | 0 | 0 | — | 0 | — | 0 | 0 | 0 | 0 | 0 | 0 | — | 0 | 0 | — | 0 | 0 | 0 | 0 | 0 |
| | | Post | 5 | 9 | 9 | 9 | 8 | 2 | 3 | — | 9 | — | 9 | 8 | 9 | 9 | 9 | — | 9 | 2 | 2 | 1 | 7 | 8 | 2 | 4 | 4 |
| 78 | 1 | Pre | 0 | 0 | 0 | 0 | 0 | 0 | 0 | — | 0 | — | 0 | 0 | 0 | 0 | 0 | 0 | — | 0 | 0 | — | 0 | 0 | 0 | 0 | 0 |
| | | Post | 5 | 9 | 9 | 9 | 8 | 3 | 4 | — | 9 | — | 9 | 7 | 8 | 9 | 9 | — | 9 | 4 | 5 | 4 | 5 | 9 | 6 | 6 | 2 |

TABLE V-continued

| COMPOUND NO. | RATE OF APPLICATION kg/ha | PRE-OR POST-EMERGENCE APPLICATION | TEST PLANTS (see Table VI) | | | | | | | | | | | | | | | | | | | | | | | | |
|---|---|---|---|---|---|---|---|---|---|---|---|---|---|---|---|---|---|---|---|---|---|---|---|---|---|---|---|
| | | | Sb | Rp | Ct | Sy | Mz | Rc | Ww | Pi | Ca | Ga | Am | Bd | Eh | Ip | Ab | Xa | Xs | Av | Al | Ag | Sh | St | Dg | Ec | Ce |
| 79 | 1 | Pre | 9 | 6 | 0 | 0 | 0 | 8 | 0 | — | 9 | — | 9 | 9 | 9 | 0 | 7 | 0 | — | 0 | 0 | — | 0 | 9 | 9 | 2 | 0 |
| | 0.25 | Post | 9 | 9 | 9 | 9 | 8 | 4 | 7 | — | 9 | — | 9 | 9 | 9 | 9 | 9 | — | 9 | 8 | 8 | 5 | 9 | 9 | 9 | 9 | 7 |
| 80 | 0.25 | Pre | 7 | 5 | 0 | 0 | 0 | 5 | 0 | — | 9 | — | 9 | 3 | 9 | 0 | 3 | 0 | — | 0 | 0 | — | 0 | 5 | — | 0 | 0 |
| | 0.0625 | Post | 9 | 9 | 9 | 9 | 6 | 3 | 3 | — | 9 | — | 9 | 9 | 9 | 9 | 9 | — | 9 | 4 | 2 | 2 | 7 | 9 | 9 | 3 | 5 |
| 81 | 0.25 | Pre | 5 | 0 | 0 | 0 | 0 | 0 | 0 | — | 9 | — | 9 | 0 | 5 | 0 | 0 | 0 | — | 0 | 0 | — | 0 | 0 | 0 | 0 | 0 |
| | 0.0625 | Post | 5 | 8 | 5 | 8 | 6 | 1 | 3 | — | 9 | — | 9 | 9 | 7 | 4 | 8 | — | 9 | 2 | 0 | 2 | 2 | 4 | 4 | 3 | 2 |
| 82 | 0.25 | Pre | 6 | 5 | 2 | 0 | 0 | 5 | 0 | — | 9 | — | 9 | 5 | 9 | 0 | 5 | 0 | — | 0 | 0 | — | 0 | 7 | 9 | 0 | 0 |
| | 0.0625 | Post | 4 | 8 | 6 | 4 | 6 | 2 | 2 | — | 9 | — | 9 | 7 | 7 | 6 | 9 | — | 3 | 0 | 1 | 2 | 3 | 8 | 2 | 1 | 3 |
| 83 | 0.25 | Pre | 4 | 2 | 0 | 0 | 0 | 0 | 6 | — | 9 | — | 9 | 0 | 0 | 0 | 0 | 0 | — | 0 | 0 | — | 0 | 0 | — | 0 | 0 |
| | 0.0625 | Post | 5 | 8 | 3 | 8 | 3 | 3 | 2 | — | 9 | — | 9 | 3 | 6 | 4 | 5 | — | 5 | 2 | 2 | 2 | 3 | 7 | 4 | 2 | 2 |
| 84 | 0.25 | Pre | 9 | 9 | 2 | 0 | 0 | 5 | 0 | — | 9 | — | 9 | 9 | 9 | 0 | 6 | 0 | — | 0 | 0 | — | 0 | 9 | — | 0 | 0 |
| | 0.0625 | Post | 9 | 9 | 9 | 9 | 8 | 4 | 3 | — | 9 | — | 9 | 9 | 9 | 9 | 9 | — | 5 | 4 | 6 | 5 | 9 | 8 | — | 9 | 3 |
| 85 | 0.25 | Pre | 9 | 9 | 1 | 0 | 0 | 9 | 0 | — | 9 | — | 9 | 8 | 9 | 0 | 7 | 0 | — | 0 | 0 | — | 1 | 9 | — | 0 | 0 |
| | 0.0625 | Post | 7 | 9 | 9 | 9 | 8 | 4 | 6 | — | 9 | — | 9 | 9 | 9 | 9 | 9 | — | 9 | 6 | 5 | 2 | 9 | 9 | — | 9 | 4 |
| 86 | 0.25 | Pre | — | — | 2 | — | 2 | — | 2 | — | 9 | — | 9 | 9 | 9 | — | 9 | 0 | — | 5 | 3 | — | 5 | 9 | — | 6 | 0 |
| | 0.0625 | Post | 9 | 9 | 9 | 9 | 5 | 8 | 9 | 9 | 9 | 9 | 9 | 9 | 9 | 9 | 9 | — | 9 | 7 | 7 | 8 | 9 | — | 9 | 5 | — |
| 87 | 0.25 | Pre | — | 0 | 0 | — | 3 | — | 2 | — | 9 | — | 9 | — | 9 | — | 9 | 0 | — | — | 5 | — | — | 9 | — | 6 | 0 |
| | | Post | 9 | 9 | 6 | 8 | 5 | 3 | 3 | 9 | 9 | 9 | 9 | 9 | 9 | 9 | 9 | — | 9 | 6 | 5 | 2 | 9 | — | 9 | 9 | — |
| 88 | 0.25 | Pre | — | — | — | — | 0 | — | 0 | — | 9 | — | 9 | — | 2 | — | 8 | 0 | — | 2 | 3 | — | — | 9 | — | 6 | 0 |
| | | Post | 9 | 9 | 9 | 6 | 5 | 5 | 3 | 9 | 9 | — | 9 | 5 | 9 | 9 | 9 | — | 9 | 5 | 9 | 4 | 9 | — | 9 | 6 | — |
| 89 | 1 | Pre | 0 | 0 | 0 | 0 | 0 | 0 | 0 | — | 5 | 0 | 5 | 0 | 0 | — | 0 | 0 | — | 0 | 0 | — | 0 | 0 | 0 | 0 | 0 |
| | 0.25 | Post | 5 | — | 9 | 6 | 3 | 2 | 0 | 5 | 9 | 5 | 5 | 6 | 9 | 8 | 6 | — | 7 | 3 | 0 | — | 5 | 3 | 2 | 3 | 2 |
| 90 | 1 | Pre | 5 | 5 | 5 | 3 | 4 | 0 | 0 | — | 9 | 0 | 9 | 6 | 7 | — | 9 | 0 | — | 0 | 0 | — | 5 | 9 | — | 2 | 0 |
| | 0.25 | Post | 9 | 9 | 9 | 9 | 6 | 3 | 4 | — | 9 | 9 | 9 | 9 | 9 | 9 | 9 | — | 9 | 5 | 5 | 5 | 9 | 9 | 9 | 5 | 3 |
| 91 | 1 | Pre | 9 | 9 | 0 | 0 | 0 | 7 | 0 | — | 9 | — | 9 | 9 | 9 | — | 9 | 0 | — | 0 | 5 | — | 7 | 9 | — | 5 | 0 |
| | 0.25 | Post | 9 | — | 9 | 9 | 7 | 2 | 9 | 9 | 9 | 9 | 9 | 9 | 9 | 9 | 9 | — | 9 | 9 | 9 | — | 9 | 9 | 9 | 7 | 4 |
| 92 | 0.25 | Pre | 5 | 2 | 0 | 0 | 0 | 0 | 3 | — | 0 | 0 | 0 | 0 | 0 | 0 | 0 | 0 | — | 7 | 0 | — | 0 | 0 | — | 0 | 0 |
| | 0.0625 | Post | 2 | 0 | 9 | 4 | — | 0 | 0 | — | 7 | 7 | 8 | 6 | 5 | 6 | 6 | — | 5 | 1 | 0 | 1 | 3 | 5 | 0 | 0 | 0 |
| 93 | 0.25 | Pre | 0 | 0 | 0 | 0 | 0 | 1 | 0 | — | 9 | 0 | — | 0 | 7 | — | 5 | 0 | — | 0 | 0 | — | 7 | 0 | — | 0 | 0 |
| | 0.0625 | | 6 | 6 | 9 | 7 | — | 0 | 1 | — | 7 | 1 | 6 | 6 | 9 | 8 | 3 | — | 3 | 7 | 2 | 3 | 5 | 7 | 6 | 1 | 1 |
| 94 | 0.25 | Pre | 9 | 5 | 0 | 0 | 0 | 8 | 0 | — | 9 | 0 | — | — | 9 | 3 | 7 | 0 | — | 7 | 1 | — | 7 | 3 | — | 0 | 0 |
| | 0.0625 | Post | 9 | 9 | 9 | 8 | — | 3 | 3 | — | 9 | 9 | 9 | 9 | 9 | 9 | 9 | — | 9 | 3 | 3 | 7 | 9 | 9 | 9 | 9 | 5 |
| 95 | 1 | Pre | 0 | 1 | 0 | 0 | 0 | 0 | 0 | — | 8 | 0 | 5 | 0 | 3 | 0 | 3 | 0 | — | 0 | 0 | — | 0 | 1 | — | 0 | 0 |
| | 0.25 | Post | 6 | 9 | 9 | 8 | 6 | 3 | 3 | — | 9 | 9 | 9 | 9 | 7 | 7 | 9 | — | 6 | 3 | 1 | 2 | 4 | 5 | 6 | 3 | 5 |

TABLE VI

| Test Plants |
|---|
| Sb - Sugar Beet |
| Rp - Rape |
| Ct - Cotton |
| Sy - Soybean |
| Mz - Maize |
| Ww - Winter wheat |
| Rc - Rice |
| Bd - *Bidens pilosa* |
| Ip - *Ipomoea lacunosa* (pre-emergence) *Ipomoea hederacea* (post-emergence) |
| Am - *Amaranthus retroflexus* |
| Pi - *Polygonum aviculare* |
| Ca - *Chenopodium album* |
| Ga - *Galium aparine* |
| Xa - *Xanthium spinosum* |
| Xs - *Xanthium strumarium* |
| Ab - *Abutilon theophrasti* |
| Eh - *Euphorbia heterophylla* |
| Av - *Avena fatua* |
| Dg - *Digitaria sanguinalis* |
| Al - *Alopecurus myosuroides* |
| St - *Setaria viridis* |
| Ec - *Echinochloa crus-galli* |
| Sh - *Sorghum halepense* |
| Ag - *Agropyron repens* |
| Ce - *Cyperus esculentes* |

We claim:

1. A compound of formula (I):

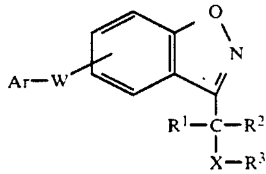

(I)

in which

Ar is an optionally substituted aryl, pyridine or pyrazole ring system;

$R^1$ and $R^2$ are independently selected from H, optionally substituted alkyl, alkenyl or alkynyl, halogen, $NR^aR^b$, or $R^1$ and $R^2$ together with the carbon to which they are attached form an optionally substituted alkenyl or cycloalkyl group;

$R^3$ is $CO_2R^4$, CN, $COR^4$, $CH_2OR_4$, $CH(OH)R^4$, $CH(OR^4)$ $R^5$, $CH_2OSO_2R^4$, $CH_2OSO_3R^4$, $CH_2ONR^6R^7$, $CSNH_2$, $COSR^4$, $CSOR^4$, $CONHSO_2R^4$, $CONR^6R^7$, $CONHNR^6R^7$, $CONHN^+R^6R^7R^8$ $Y^-$, $CO_2^-M^+$ OR $COON{=}CR^6R^7$;

$M^+$ is an agriculturally acceptable cation;

$Y^-$ is an agriculturally acceptable anion;

$R^4$ and $R^5$ are independently selected from H or an optionally substituted alkyl, aryl, alkenyl or alkynyl group;

$R^6$, $R^7$, $R^8$, $R^9$, $R^a$ and $R^b$ are independently selected from H or an optionally substituted alkyl, alkenyl, aryl or alkynyl group or any two of $R^6$, $R^7$, $R^8$, $R^9$, $R^a$ and $R^b$ together with the atom to which they are attached form a cycloalkyl, pyrrolidine, piperidine or morpholine ring;

$R^6$ and $R^7$ may also be a pyridine or pyrazole ring;

W is O or $NR^{10}$ where $R^{10}$ is H or $C_1$-$C_3$ alkyl;

X is $(CH_2)_n$, CH=CH, $CH(OR^c)CH_2$, or $COCH_2$; where $R^c$ is H or an optionally substituted alkyl, aryl, alkenyl or alkynyl group; and n is 0, 1 or 2;

wherein optional substituents for aryl and heterocyclic rings are up to 5 members selected from halogen, $C_1$-$C_3$ alkyl, $C_1$-$C_{10}$ haloalkyl, $C_1$-$C_{10}$ haloalkoxy, nitro, cyano, $C_1$-$C_3$ alkoxy, and $S(O)_pR^d$ where p is 0, 1 or 2 and $R^d$ is $C_1$-$C_{10}$ alkyl;

optional substituents for alkyl, alkenyl and alkynyl groups are one or more groups selected from halo; nitro; cyano; phenyl; $CO_2R^{11}$, $NHCOR^{11}$ or $NHCH_2COR^{11}$ wherein $R^{11}$ is hydrogen, $C_1$-$C_6$ alkyl, or an agriculturally acceptable cation; $C_1$-$C_6$ alkoxy; oxo; $S(O)_pR^d$ where p and $R^d$ are as defined above; amino; mono- and di-$(C_1$-$C_6)$alkylamino; $CONR^{12}R^{13}$ where $R^{12}$ and $R^{13}$ are independently hydrogen, $C_1$-$C_6$ alkyl, $C_2$-$C_6$ alkenyl or $C_2$-$C_6$ alkynyl;

agriculturally acceptable cations are selected from sodium, potassium, calcium, and sulphonium or sulphoxonium ions having the formula $S^+(O)_qR^6R^7R^8$ where q is 0 or 1 and ammonium or tertiary ammonium ions having the formula $N^+R^6R^7R^8R^9$; and agriculturally acceptable anions are selected from halides, tetrafluoroborate, mesylate and tosylate ions.

2. A compound according to claim 1 where Ar is optionally substituted phenyl, optionally substituted pyridyl or optionally substituted pyrazolyl.

3. A compound according to claim 1 or claim 2 where W is O.

4. A compound according to claim 1 where $R^3$ is $CO_2R^4$, CN, $CH_2OR^4$, $CSNH_2$, $CONR^6R^7$, $CONHNR^6R^7$, $CONHN^+R^6R^7R^8$ $Y^-$, $COON{=}CR^6R^7$ or $CO_2^-M^+$

5. A compound according to claim 1 where Ar is:

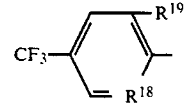

where $R^{18}$ is N, CH or $CR^{20}$ and $R^{19}$ and $R^{20}$ are independently selected from halogen.

6. A compound according to claim 1 where $R^3$ is $CO_2R^4$, CN, $CONR^6R^7$ or $COON{=}CR^6R^7$.

7. A compound according to claim 1 where $R^3$ is $CO_2R^4$.

8. A compound of formula (ID)

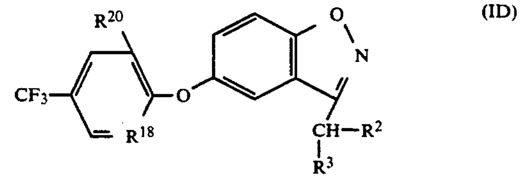

(ID)

where $R^{18}$ and $R^{20}$ are as defined in claim 5 and $R^2$ and $R^3$ are as defined in claim 1.

9. A herbicidal composition comprising a compound of formula (I) as defined in claim 1 in combination with a carrier or diluent.

10. A method of killing or controlling the growth of unwanted plants which method comprises applying to the plants or to a locus thereof an effective amount of a compound of formula (I) as defined in claim 1.

* * * * *